US012788472B2

(12) United States Patent
Gorin et al.

(10) Patent No.: US 12,788,472 B2
(45) Date of Patent: Nov. 10, 2026

(54) IMPEDANCE MATCHING IN ELECTROSURGERY

(71) Applicant: Applied Medical Resources Corporation, Rancho Santa Margarita, CA (US)

(72) Inventors: Igor Gorin, Rancho Santa Margarita, CA (US); Matthew Carter, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 252 days.

(21) Appl. No.: 18/512,544

(22) Filed: Nov. 17, 2023

(65) Prior Publication Data

US 2024/0173064 A1 May 30, 2024

Related U.S. Application Data

(60) Provisional application No. 63/426,066, filed on Nov. 17, 2022.

(51) Int. Cl.

| | |
|---|---|
| ***A61B 18/12*** | (2006.01) |
| *A61B 18/00* | (2006.01) |
| *H03H 7/38* | (2006.01) |

(52) U.S. Cl.

CPC ..................... *A61B 18/1233* (2013.01); *A61B 2018/00642* (2013.01); *A61B 2018/0072* (2013.01);

(Continued)

(58) Field of Classification Search

CPC ...... A61B 18/1233; A61B 2018/00642; A61B 2018/0075; H03H 7/38

See application file for complete search history.

(56) References Cited

U.S. PATENT DOCUMENTS 5,424,691 A * 6/1995 Sadinsky ................. H03H 7/40 333/17.3

2009/0182323 A1* 7/2009 Eder .................. A61B 18/1442 606/50

(Continued)

FOREIGN PATENT DOCUMENTS

WO WO 2015/023899 A2 2/2015

OTHER PUBLICATIONS

European Patent Office, The International Search Report and Written Opinion for International Application No. PCT/US2023/080247, entitled “Impedance Matching Electrosurgery,” mailed Mar. 18, 2024, 24pgs.

(Continued)

*Primary Examiner* — Sean W Collins

(74) *Attorney, Agent, or Firm* — Shirin Bozorgui; Patrick Ikehara

(57) ABSTRACT

Systems and methods for performing impedance matching to enhance surgical outcomes in an electrosurgical system are described. An impedance matching network is interposed along a path of RF energy and matches dynamically an output impedance of an electrosurgical generator to an input impedance of the tissue load by varying the inductance of a resonant cell. As a result, an adjustment is made to the output phase of the electrosurgical generator to ensure an optimal matching of the source and load impedances based on sealing, fusing or cutting cycle of the tissue. This leads to a resonance condition which provides a zero-degrees phase shift between the RF output voltage and current of the electrosurgical generator. The inductance of the resonant cell is proportional to either the magnitude of the current flowing through DC windings of a saturable core reactor or on the size of an airgap in the inductor core material.

14 Claims, 11 Drawing Sheets

(52) U.S. Cl.
CPC ................. *A61B 2018/0075* (2013.01); *A61B 2018/00767* (2013.01); *A61B 2560/02* (2013.01); *A61B 2560/04* (2013.01); *H03H 7/38* (2013.01)

(56) References Cited

U.S. PATENT DOCUMENTS

| | | | | |
|---|---|---|---|---|
| 2013/0267943 | A1 | 10/2013 | Hancock | |
| 2015/0051750 | A1* | 2/2015 | Kurs ....................... | G05F 1/625 700/298 |

OTHER PUBLICATIONS

The International Bureau of WIPO, International Preliminary Report on Patentability for International Application No. PCT/US2023/080247, entitled “Impedance Matching in Electrosurgery,” dated May 30, 2025, 16 pgs.

* cited by examiner

IMPEDANCE MATCHING IN ELECTROSURGERY

CROSS-REFERENCE TO RELATED APPLICATIONS

This application claims priority to and benefit of U.S. Provisional Patent Application Ser. No. 63/426,066 entitled "Impedance Matching in Electrosurgery" filed on Nov. 17, 2022, which is hereby expressly incorporated by reference in its entireties for all purposes.

TECHNICAL FIELD

The present invention generally relates to electrosurgical systems, and in particular, to systems and methods for controlling the energy transfer efficiency between an electrosurgical generator and tissue impedance load or tissue load.

BACKGROUND

Electrosurgery is surgery using electrosurgical energy that involves the application of high voltage, high frequency electrical energy, e.g., radiofrequency (RF) energy, to tissue for the purpose of sealing, fusing and/or cutting tissues or vessels. Electrosurgery typically utilizes an electrosurgical generator to generate the RF energy and electrosurgical hand devices or instruments that direct the RF energy to the target tissue. Electrosurgical instruments generally fall within two classifications: monopolar and bipolar. In monopolar instruments, electrical energy is supplied to one or more electrodes on the instrument with high current density while a separate return electrode is electrically coupled to a patient and is often designed to minimize current density. Bipolar electrosurgical instruments, which operate without separate return electrodes, can deliver electrical signals to a focused tissue area with reduced risks.

One common concern in the management of the electrosurgical energy is impedance matching. In order to maximize the power transferred from a source to a load, the output impedance of the source should equal the input impedance of the load. Failure to match impedances may lead to signal reflection and inefficient power transfer. Excessive power loss, heat dissipation, and even circuit failure may all result from improper impedance matching. In these cases, reduced efficiency is a result of improper matching, which causes excessive power loss. On the other hand, accurate, balanced impedance matching may lead to the desired maximum power transfer and/or power efficiency.

In the case of electrosurgery, while the RF energy is applied to the target tissue, the target tissue is affected and its characteristics, i.e., input impedance load, changes as a result of the application of the RF energy. When the load impedance changes, a greater portion of power is reflected which may represent a substantial impedance mismatch and inefficient power transfer. Under high RF output power conditions during electrosurgery sealing events, the efficiency of energy transfer from the electrosurgical generator to the tissue is lower than desired. Efficient energy delivery to the tissue can be useful for improving the seal quality, seal consistency and lowering power requirements for sealing tissue. Hence, embodiments of the present invention are intended to maximize or at least improve the power transfer efficiency between an electrosurgical generator and the tissue load in surgical procedures.

SUMMARY

In accordance with various embodiments, this disclosure describes systems and methods for performing impedance matching to enhance surgical outcomes. The systems and methods allows for matching the source and load impedances under all dynamic conditions, such as variable loads, procedural, and/or operational conditions. This ensures optimal matching based on the sealing, fusing, or cutting cycle of the tissue, thereby achieving improved surgical results.

In accordance with one aspect of the present invention, an electrosurgical system for performing surgical procedures is provided. The electrosurgical system may include an electrosurgical generator configured to supply RF energy to a surgical site and an electrosurgical instrument. The electrosurgical instrument having at least one active electrode adapted to treat tissue with the supplied RF energy. The electrosurgical system may further include an impedance matching network. The impedance matching network in various embodiments may include a tunable resonant cell interposed along a path of RF energy and arranged to provide maximum power transfer from the electrosurgical generator to the electrosurgical instrument. This maximum power transfer in various embodiments is achieved by varying dynamically an inductance of the tunable resonant cell to create a resonant condition, thereby adjusting a phase of the supplied RF energy to a predetermined phase value.

In accordance with a second aspect of the present invention a method for performing impedance matching in electrosurgical procedures is provided. The method includes the steps of: providing an electrosurgical generator to supply RF energy to a surgical site via an electrosurgical instrument; interposing a tunable resonant cell along a path of RF energy to provide maximum power transfer from the electrosurgical generator to the surgical instrument; and selectively controlling an inductance of the tunable resonant cell to adjust a phase of the supplied RF energy to a predetermined phase value.

In accordance with a third aspect of the present invention, an electrosurgical system is provided. The electrosurgical system may include an electrosurgical generator configured to supply RF energy and an electrosurgical instrument operatively coupled to the electrosurgical generator to treat a target tissue. The electrosurgical system further includes an impedance matching network coupled between the electrosurgical generator and the electrosurgical instrument. The impedance matching network, according to the embodiments of the present invention, may include a first E-shaped magnetic core having a central leg and two outer legs and a second E-shaped magnetic core having a central leg and two outer legs. The first and second E-shaped magnetic cores in various embodiments are arranged in a mirror-image configuration such that the central leg and the two outer legs from each of the first and second E-shaped magnetic cores are aligned and facing each other.

In accordance with a fourth aspect of the present invention, there is provided an electrosurgical system that includes a controller and an impedance matching network. In various embodiments, the controller is configured to receive measured voltage and current values of a supplied RF energy and calculate the phase difference between these measured values. The controller is further configured to determine a phase error with respect to a predetermined phase value and output an impedance matching control signal in response to the determined phase error. The impedance matching network is configured to receive the impedance matching control signal. In accordance with various embodiments, the impedance matching network may include a saturable core reactor (SCR) having a pair of E-shaped magnetic cores arranged in a mirror-image configuration. The impedance matching network further includes an AC winding, wound around a central leg of the pair of E-shaped magnetic cores, and is configured to have a variable inductance in accordance with the impedance matching control signal.

In accordance with a fifth aspect of the present invention, there is provided an electrosurgical system having an electrosurgical generator configured to supply RF energy and an electrosurgical instrument operatively coupled to the electrosurgical generator to treat a target tissue. The electrosurgical system further includes an impedance matching network coupled between the electrosurgical generator and the electrosurgical instrument. In accordance with various embodiments, the impedance matching network may include a first E-shaped magnetic core having a central leg and two outer legs and a second E-shaped magnetic core having a central leg and two outer legs. The first and second E-shaped magnetic cores are arranged in a mirror-image configuration such that the central leg and the two outer legs from each of the first and second E-shaped magnetic cores are aligned and facing each other. This arrangement forms in various embodiments a symmetrical structure having two identical halves that are separated by an airgap.

In accordance with a sixth aspect of the present invention, there is provided an electrosurgical system having a controller and an impedance matching network. The controller in various embodiments is configured to: receive measured voltage and current values of a supplied RF energy; calculate a phase difference between the measured voltage and current values of the supplied RF energy; determine a phase error with respect to a predetermined phase value; and output an impedance matching control signal in response to the phase error. The impedance matching network in various embodiments may include a variable core inductor (VCI) having a pair of E-shaped magnetic cores arranged in a mirror-image configuration. The impedance matching network further includes a single winding that is wound around a central leg of the pair of E-shaped magnetic cores, and is configured to have a variable inductance in accordance with the impedance matching control signal. The impedance matching network is further configured to receive the impedance matching control signal.

In accordance with one other aspect of the present invention, an impedance matching circuitry for use in an electrosurgical system is provided. The impedance matching circuitry may include a first E-shaped magnetic core having a central leg and two outer legs, a second E-shaped magnetic core having a central leg and two outer legs and a plurality of windings. The first and second E-shaped magnetic cores in various embodiments are arranged in a mirror-image configuration such that the central leg and the two outer legs from each of the first and second E-shaped magnetic cores are aligned and facing each other. The plurality of windings may include one AC windings wound around the central leg of the mirror-image configuration and two DC windings where one DC winding is wound around each outer leg of the mirror image configuration. The inductance of the AC winding according to the embodiments of the present invention is selectively controllable based on a DC current flowing through the two DC windings.

In accordance with another aspect of the present invention, an impedance matching circuitry for use in an electrosurgical system is provided. The impedance matching circuitry may include a first E-shaped magnetic core having a central leg and two outer leg, a second E-shaped magnetic core having a central leg and two outer legs, and a single winding wound around the central leg of the mirror-image configuration. The first and second E-shaped magnetic cores are arranged in a mirror-image configuration such that the central leg and the two outer legs from each of the first and second E-shaped magnetic cores are aligned and facing each other, forming a symmetrical structure with two identical halves that are separated by an airgap. In accordance with various embodiments, an inductance of the single winding is selectively controllable based on variations in the size of the airgap achieved by moving one of the two identical halves relative to the other.

Many of the attendant features of the present invention will be more readily appreciated as the same becomes better understood by reference to the foregoing and following description and considered in connection with the accompanying drawings.

BRIEF DESCRIPTION OF THE DRAWINGS

The present disclosure is described in conjunction with the appended figures.

Figure 1:
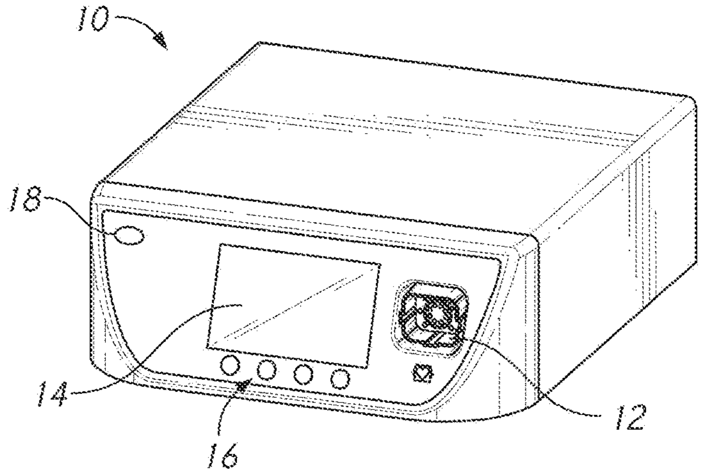
FIG. 1 illustrates a perspective view of an electrosurgical generator in accordance with various embodiments of the present invention.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the first same reference label irrespective of the second reference label.

DETAILED DESCRIPTION

The ensuing description provides exemplary embodiment(s) only, and is not intended to limit the scope, applicability or configuration of the disclosure. Rather, the ensuing description of the exemplary embodiment(s) will provide those skilled in the art with an enabling description for implementing exemplary embodiments of the disclosure. It should be understood that various changes may be made in the function and arrangement of elements without departing from the spirit and scope of the invention.

This disclosure relates in general to electrosurgery and electrosurgical systems. It specifically relates to systems and methods of impedance matching to control the energy transfer efficiency between an electrosurgical generator and a target tissue.

Embodiments of the present invention are directed to systems and methods for enhancing surgical outcomes by providing an impedance matching network that is capable of accommodating changing tissue impedances occurring during electrosurgical procedures. The present invention in accordance with various embodiments allows for matching source impedances to load impedances under all dynamic conditions such as, for example, varying tissue impedance load due to electrosurgical operations or tissue affects and any operational conditions and commands determined by the surgeon, surgical procedure and/or device script. The impedance matching network according to the embodiments of the present invention is interposed along a path of RF energy and matches dynamically the output impedance of the source energy, e.g., electrosurgical generator, to the input impedance of the load, e.g., tissue impedance load or tissue load.

To achieve maximum power delivery, any reactive components present in the load, should be of equal magnitude but opposite sign of the source impedance. In other words, the source and load impedances should be complex conjugates of each other in order to achieve maximum power delivery and to improve power efficiency. The impedance matching network in accordance with various embodiments of the present invention may include an LC resonant circuit with an adjustable inductor. The adjustable inductor in various embodiments may include a saturable core reactor (SCR) coupled in series with one one or more capacitors that are electrically connected to one another. The saturable core reactor (SCR) according to the embodiments of the present invention allows for not only preliminary matching source impedances to load impedances, but also for accommodating constantly changing tissue load impedances under any varying conditions during electrosurgical operations.

In the following, the electrosurgical system and method according to various embodiments of the present invention is explained in detail with sections individually describing: the electrosurgical generator, the electrosurgical hand device or instrument and the control system and method used for impedance matching to maximize power transfer and/or power transfer efficiency between the electrosurgical generator and target tissue.

Figure 2:
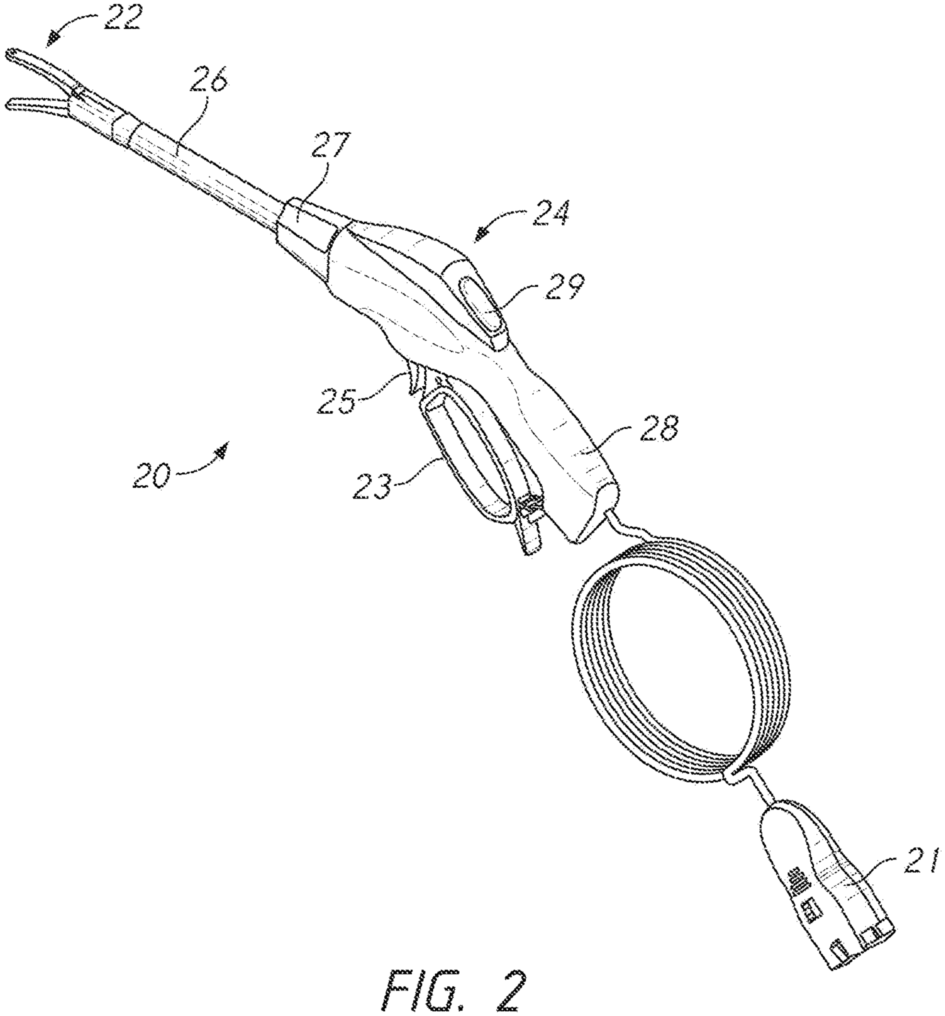
FIG. 2 illustrates a perspective view of an electrosurgical hand device in accordance with various embodiments of the present invention.

Referring first to FIGS. 1-2, an exemplary embodiment of an electrosurgical system according to various embodiments of the present invention is illustrated. As shown in these figures, the electrosurgical system may include an electrosurgical generator 10 and a removably connectable electrosurgical tool or instrument 20. The electrosurgical hand device or instrument 20 can be electrically coupled to the generator 10 via a cabled connection with a device key or connector 21 extending from the instrument 20 to a device connector or access port 12 on the generator 10. The electrosurgical instrument 20 may include audio, tactile and/or visual indicators to apprise a user of a particular or predetermined status of the instrument 20 such as, for example, a start and/or end of a fusion operation. In some embodiments, a manual controller such as a hand or foot switch can be connectable to the generator 10 and/or instrument 20 to allow predetermined selective control of the instrument such as to commence a fusion operation.

In accordance with various embodiments, the electrosurgical generator 10 includes a display 14 that may indicate the status of the electrosurgical system including, among other information, the status of the one or more electrosurgical instruments and/or accessories, connectors or connections thereto, the state or operations of the generator and error indicators. The electrosurgical generator 10 in accordance with various embodiments of the present invention may include a user interface such as, for example, a plurality of buttons 16. The plurality of buttons 16 allows for user interaction with the electrosurgical generator 10. This user interaction may include, for example, requesting an increase or decrease in the electrical energy supplied to one or more instruments 20 that are coupled to the electrosurgical generator 10. In various embodiments, the generator 10 further includes a user-accessible power-on switch or button 18 that when activated powers the generator 10 and activates or initiates a self-verification system test of the generator. In other embodiments, the display 14 can be a touch screen display thus integrating data display and user interface functionalities.

In accordance with various embodiments, once the generator 10 is activated by the activation of the power-on switch 18, the generator 10 initiates or activates a power on self-verification system test. During the self-verification system test, the generator 10 verifies regulation of the RF output in one or more RF modes and/or one or more RF resolution settings. In accordance with various embodiments, the RF regulation modes include voltage, current and power regulation modes and the RF resolution settings include low, normal and high voltage settings. The self-verification system test in various embodiment allows for rapidly identifying a potential generator issue or error prior to any use of a connected electrosurgical instrument or supply of any RF energy to the tissue or vessel through the electrosurgical instrument 10. For this purpose, one or more internal impedance loads are integrated within the electrosurgical generator 10. The internal impedance loads with multiple configurations are utilized to verify the voltage, current, power, and/or phase measurements of the generator across a plurality of RF regulation modes and a plurality of RF resolution settings. For a detailed discussion of the self-verification system test of the electrosurgical generator 10, reference may be made to U.S. patent application Ser. No. 16/562,122, filed on Sep. 5, 2019, the content of which is incorporated by reference herein in its entirety.

In various embodiments, the electrosurgical generator 10 of the present invention is configured to output radiofrequency (RF) energy through the connectable electrosurgical instrument or hand device 20 to seal, fuse and/or cut tissue or vessels via one or more electrodes. The electrosurgical generator 10, according to the embodiments of the present invention, is configured to generate up to 300V, 8 A, and 375 VA of RF energy and it is also configured to determine a phase angle or difference between RF output voltage and RF output current of the generator during activation or supply of RF energy. In this way, the electrosurgical generator 10 regulates voltage, current and/or power and monitors RF energy output (e.g., voltage, current, power and/or phase). In one embodiment, the generator 10 may stop, terminate or otherwise disrupt RF energy output under predetermined conditions. By way of example, these predetermined conditions may be any of the following conditions: when a device switch is de-asserted (e.g., fuse button released), a time value is met, and/or active phase angle and/or change of phase is greater than or equal to a phase and/or change of phase stop value indicating end of an operation such as fusion or cutting of tissue.

The electrosurgical instrument 20, according to the embodiments of the present invention, may include an elongate shaft 26 having a proximal end coupled to or from which an actuator 24 extends and a distal end coupled to or from which jaws 22 extend. A longitudinal axis extends from the proximal end to the distal end of the elongate shaft 26. In one embodiment, the actuator 24 may include a movable handle 23 which is pivotably coupled to a stationary handle or housing 28. The movable handle 23 is coupled to the stationary handle or housing 28 through a central or main floating pivot. In operation, the movable handle 23 is manipulated by a user, e.g., a surgeon, to actuate the jaws 22 at the distal end of the elongate shaft 26, and thereby, selectively opening and closing the jaws 22. When tissue or vessels are grasped between the jaws 22, a switch or button 29 is activated by the surgeon to seal, fuse and/or cut the tissue/vessels between the jaws 22. Once the button 29 is activated, associated circuitry or contacts are connected to connect appropriate electrodes of the jaws with associated connections of the generator 10 to supply RF energy to tissue grasped between the jaws 22 or otherwise in contact with the one or more electrodes of the jaws.

In various embodiments, the electrosurgical instrument 20 further includes a mechanical or electrical cutting blade that can be coupled to a blade actuator such as a blade lever or trigger 25 of the stationary handle or housing 28. The cutting blade is actuated by the blade trigger 25 to divide or cut the tissue between the jaws 22. In various embodiments, a blade slider is connected to the blade trigger 25 and a protrusion extends from a proximal portion of the blade slider into an opening in one end of the blade trigger connecting the components together. The other end of the blade trigger is exposed and accessible by the user with the blade trigger 25 being pivotable about a trigger pivot at or near the mid-point of the blade trigger. As such, as the blade trigger 25 is pulled or rotated by the user proximally, the end of the blade trigger connected to the blade slider slides or moves the blade slider distally. Integrated with or attached to a distal end of the blade slider is a cutting blade, knife or cutting edge or surface. As such, as the blade slider translates longitudinally through a blade channel in the jaws, tissue grasped between the jaws 22 is cut.

In one embodiment, the cutting edge or surface is angled to facilitate cutting of the tissue between the jaws 22. In various embodiments, the cutting blade is a curved blade, a hook, a knife, or other cutting element that is sized and configured to cut tissue between the jaws 22. In accordance with various embodiments, the elongate shaft 26 comprises an actuation tube or rod coupling the jaws 22 with the actuator. In one embodiment, the actuator includes a rotation shaft assembly including a rotation knob 27 which is disposed on an outer cover tube of the elongate shaft 26. The rotation knob 27 allows a surgeon to rotate the shaft of the device while gripping the actuator. In various embodiments, the elongate shaft 26 is rotatable 360 degrees and in other embodiments, rotation of the elongate shaft 26 is limited to 180 degrees, i.e., ninety degrees clockwise and ninety degrees counter clockwise.

Figure 3:
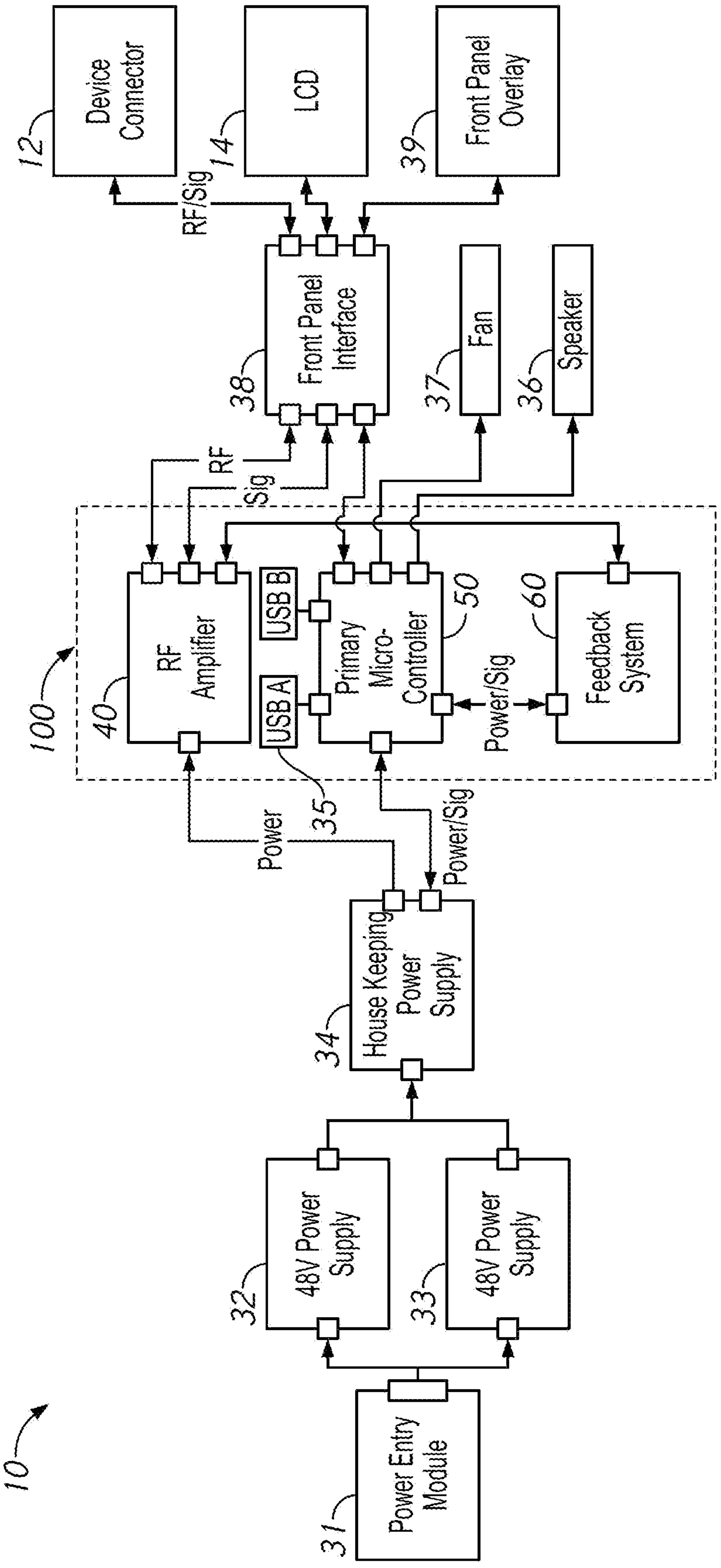
FIG. 3 depicts a block diagram of an electrosurgical generator in accordance with various embodiments of the present invention.

Referring next to FIG. 3, a block diagram of an electrosurgical generator 10 according to the embodiments of the present invention is shown. As shown in this figure, the electrosurgical generator 10 may include a power entry module 31, e.g., an AC main input, coupled to a power supply module, e.g., two 48V DC power supplies 32, 33. The power supply module converts the AC voltage from the AC main input to a DC voltage and via a house keeping power supply 34 provides power to various circuitry of the generator 10 and in particular supplies power to an RF amplifier 40 that generates or outputs the RF energy. In one embodiment, the RF amplifier 40 may include a combined Buck and H-Bridge circuitry to convert a DC voltage input into an RF output and in another embodiment into a variable amplitude 350 kHz sine wave. The DC voltage input is a 96V DC input that is generated by the two 48V DC power supplies 32, 33 coupled in series. One of the 48V DC power supply 32, 33 is configured to generate low voltage rails and in particular supply standby voltage to power on the generator 10.

The RF output and in various embodiments the amplitude of the RF waveform output is controlled and regulated by an electrosurgical control system or a digital integral servo control system 100 embedded or integrated within the electrosurgical generator 10. As shown in FIG. 3, the control system 100 may include the RF Amplifier 40, a primary microcontroller 50 and a feedback system 60. The control system 100 varies between regulating voltage, current, or power of the RF output generated by the RF Amplifier 40. In various embodiments, the feedback system 60 measures the RF output and, after processing the measured data, digitally feeds the RF output's real and imaginary components to the primary microcontroller 50. The primary microcontroller 50, according to the embodiments of the present invention, processes the received data from the feedback system 60 and adjusts the output of the RF amplifier 40 to meet a desired regulation target. In various embodiments, the feedback system 60 comprises of analog input, digital processing and digital output.

In accordance with various embodiments of the present invention, the electrosurgical generator 10 is further configured to provide RF output in three resolution settings or modes: low voltage, medium voltage and high voltage ranges. During a high voltage range or resolution setting, the RF output may reach up to 300V or 4 A and is mainly used in tissue cutting. During a medium or normal voltage range or resolution setting, the RF output may reach up to 150V or 8 A and is mainly used in tissue sealing. During the low voltage mode or resolution setting, the RF output is limited to 10V and 100 mA and is mainly used in passive tissue impedance evaluations and measurements at a level that does not create a physiological response in tissue, but is sufficient to detect open and/or short loads in the RF output path upon activation of electrosurgical hand devices, e.g., instrument 20.

In various embodiments, device scripts stored and located on connectable electrosurgical hand devices, e.g., instrument 20, and/or connectors coupled thereto, e.g., device key 21, are used to determine or set the RF output or voltage mode. The device script in various embodiments represents a procedural walkthrough of a surgical operation that may include the application and termination of RF energy to the tissue. In various embodiments, the electrosurgical generator 10 logs all RF output data onto an internal memory device, e.g., a secure digital (SD) or non-volatile memory card. The memory device is configured to be read through an interface port 35, e.g., a universal serial bus (USB) port, on the electrosurgical generator 10 (best shown in FIG. 3). In various embodiments, the generator 10 is configured to copy the data from the internal memory device to a connectable portable storage device, e.g., a USB flash drive, through the interface port of the generator.

In various embodiments, the electrosurgical generator 10 is configured to alert the surgeon when the vessel has reached a completed procedure state, e.g., a completed seal state, or if an error or fault condition has occurred. The electrosurgical generator 10 in various embodiments may include visual, tactile and/or audible outputs to provide such alerts or other indicators or information to the surgeon as dictated by the surgical procedure, device script or health or operational information regarding the device 20 and/or generator 10. In one embodiment, the generator 10 via a front panel interface 38 alerts the surgeon through the LCD display 14, which is integrated into a front panel of the generator, and in various embodiments provides specific audible alarm or informational tones through a speaker 36 also integrated into the front panel of the generator. The generator 10 in various embodiments may include a front panel overlay 39 that provides a user interface or access including navigational push buttons to allow user access to systems settings such as volume or display brightness. The front panel overlay 39 may also include the system power button or connection. In various embodiments, a fan system 37 is provided to assist in heat dissipation. Additionally, as illustrated in the FIG. 3, signal or sig represents connections that, for example, comprise of digital signals used to communicate information across systems and/or printed circuit boards, power represents connections that, for example, comprise of voltage rails used to power systems and/or printed circuit boards and RF represents connections that, for example, comprise of high voltage, high current RF energy used to seal, fuse or cut tissue or vessels.

Figure 4:
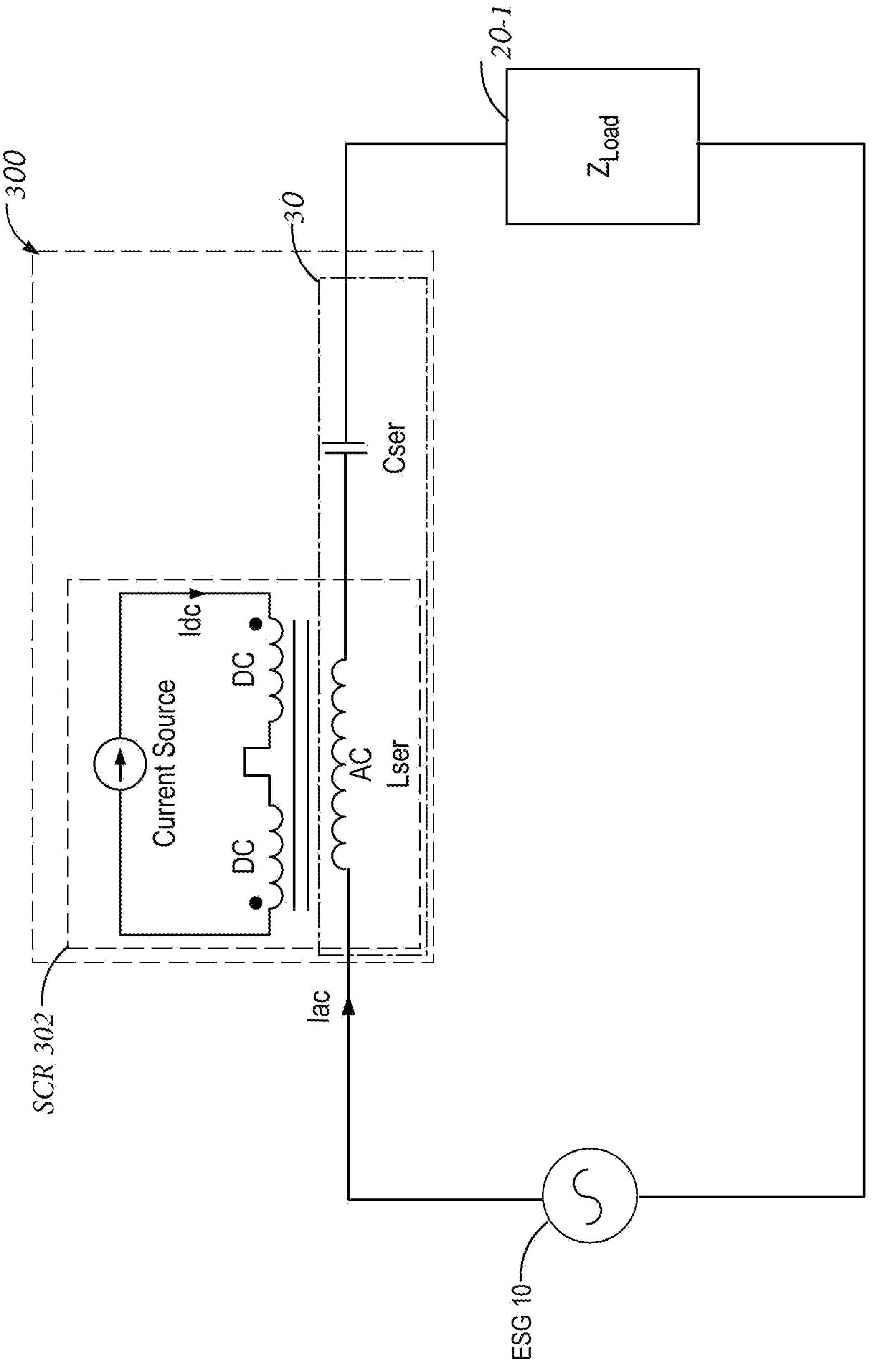
FIG. 4 illustrates a schematic diagram of an electrosurgical system depicting, in greater detail, an embodiment of an impedance matching network according to the embodiments of the present invention.

With reference to FIG. 4, a schematic diagram of an electrosurgical system depicting, in greater detail, an embodiment of an impedance matching network 300 according to the embodiments of the present invention is shown. As can be seen from this figure, the impedance matching network 300 is interposed along a path of RF energy between the electrosurgical generator 10 and the complex tissue impedance load or tissue load, e.g., $Z_{Load}$ 20-1 which is an equivalent electrical circuit of the contact between the instrument 20 with the patient's body or surgical site. Since the tissue impedance load or tissue load $Z_{Load}$ 20-1 is continuously changing due to various tissue conditions, operational conditions, and commands determined by the surgeon, surgical procedures and/or device script, the impedance matching network 300 according to the embodiments of the present invention is designed and configured to match dynamically the output impedance of the electrosurgical generator 10 to the input impedance of the tissue load, e.g., $Z_{Load}$ 20-1. For this purpose, the impedance matching network 300 in accordance with various embodiments may include an LC resonant circuit, e.g., a series LC tank circuit 30, having an adjustable inductor ($L_{Ser}$) coupled in series with a capacitor bank ($C_{Ser}$). In various embodiments, the adjustable inductor may include a saturable core reactor (SCR) 302 that is electrically coupled with one or more capacitors 304 (not shown in FIG. 4) to form a variable resonant cell, e.g., series LC tank or resonant circuit 30. The inductance of the saturable core reactor (SCR) 302 in accordance with various embodiments of the present invention is dynamically adjusted to control the energy transfer efficiency between the electrosurgical generator 10 and the tissue impedance load or tissue load $Z_{Load}$ 20-1.

Figure 5:
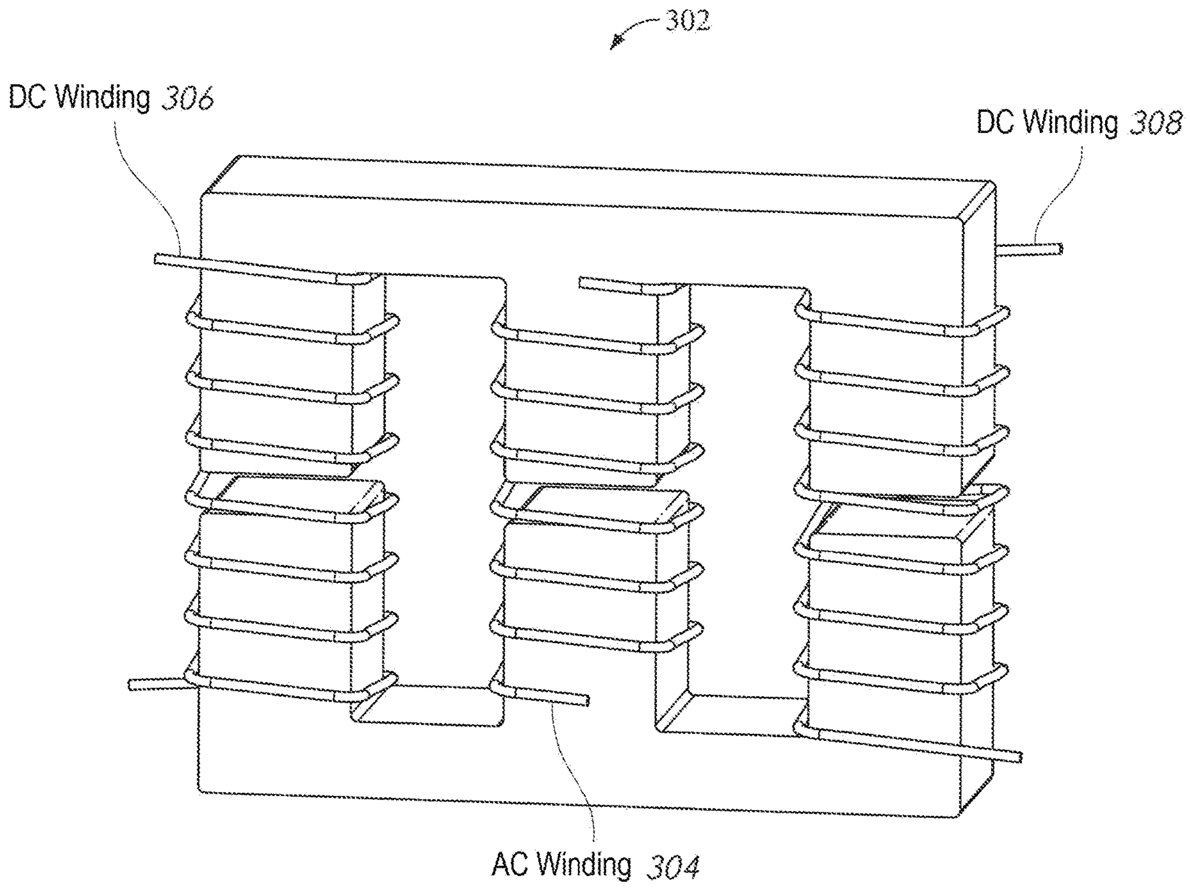
FIG. 5 depicts a schematic illustration of an embodiment of a saturable core reactor (SCR) according to the embodiments of the present invention.

Referring now to FIG. 5, a schematic illustration of an embodiment of a saturable core reactor (SCR) 302 in accordance with various embodiments of the present invention is shown. As can be seen from this figure, the saturable core reactor 302 may include a pair of E-shaped magnetic cores or E-cores. Each E-shaped magnetic core or E-core consists of one central leg and two individual outer legs. The two E-shaped magnetic cores or E-cores in various embodiments are disposed such that the central leg and the two outer legs from each core are aligned and facing each other. This results in a symmetrical or mirror-image configuration formed by two identical magnetic core halves. The saturable core reactor (SCR) 302 in accordance with various embodiments may have three windings: one AC load winding and two DC control windings. As shown in FIG. 5, the two DC control windings and the one AC load winding are interlinked by the pair of E-shaped magnetic cores or E-cores such that when assembled, the magnetic cores create a continuous magnetic path. The use of E-shaped magnetic cores strengthens the magnetic field while offering a more symmetric solution to form a closed magnetic system. The amount of increase in the magnetic field by the E-cores may depend on the magnetic permeability of the core material. In various embodiments, the E-cores material are made from ferrite or silicone steel. In some embodiments, powdered cores which consist of metal grains mixed with a suitable organic or inorganic binder, and pressed to a desired density, are used as the E-core material. In other embodiments, carbonyl iron powders are used as the E-core material.

The AC load winding in accordance with various embodiments of the present invention is wound around the center leg of the pair of E-shaped magnetic cores or E-cores. In various embodiments, the AC load winding is designed to act as the inductor ($L_{Ser}$) in the series LC tank or resonant circuit 30 that is interposed along the path of RF energy between the electrosurgical generator 10 and the complex tissue impedance load or tissue load $Z_{Load}$ 20-1. On the other hand, the two DC control windings are designed and configured to control the inductance of the AC load winding. For this purpose, one DC control winding is wound around each outer leg of the pair of E-shaped magnetic cores or E-cores. As it can be seen from FIGS. 4-5, the two DC control windings are wound in opposite directions, resulting in inverse polarities. This configuration serves to obviate or at least alleviate electromagnetic interference. Additionally, the two DC windings are electrically connected in series and linked to a DC current source. It should be also noted that the distance or airgap between the two E-shaped magnetic cores (E-cores) is designed to enhance magnetic isolation, thereby preventing magnetic interference between the windings on each core.

Despite constant changes in the tissue impedance load, the saturable core reactor (SCR) 302 tends to maintain a given magnitude of current in the AC load winding. This is achieved by adjusting the magnitude of DC current passing in the DC control winding. When the current through the two DC control windings reaches a certain current threshold, the E-cores of the saturable core reactor (SCR) begin to saturate. As the E-cores are pushed further and further into saturation, the relative permeability of the magnetic material, μ, decreases, thereby decreasing the inductance of the AC load winding (i.e., $L_{Ser}$). As such, the inductance of the AC load winding ($L_{Ser}$) is directly proportional to the magnitude of the current passing through the DC control winding. In operation, in order to match the impedance of the tissue impedance load or tissue load to that of the electrosurgical generator, the inductance of the AC load winding is constantly adjusted as a function of the current passing through the DC control winding. This makes the source impedance or output impedance of the electrosurgical generator dependent on the series LC tank or resonant circuit 30 of the impedance matching network 300.

On the other hand, the tissue impedance load or tissue load $Z_{Load}$ 20-1 is continuously changing under various surgical, operational or procedural conditions. In various embodiments, the dynamically changing tissue impedance load or tissue load may be more inductive or capacitive in nature due to electrosurgical tissue effects, e.g., sealing, fusing or cutting cycle of the tissue or any other operational or procedural conditions. As such, there will be a difference in impedance values of the electrosurgical generator and the tissue impedance load at any given sealing cycle of tissue. This difference in impedance values leads in turn to a phase difference between the RF output voltage and current of the generator. The electrosurgical generator 10 in various embodiments is configured to continuously monitor and measure the phase difference between voltage and current delivered across the tissue impedance load or tissue load $Z_{Load}$ 20-1. A positive phase difference (current lagging voltage) indicates a more inductive tissue impedance load or tissue load while a negative phase difference (current leading voltage) implies a more capacitive tissue load.

The saturable core reactor (SCR) 302 in accordance with various embodiments of the present invention continuously matches the output impedance of the electrosurgical generator to the input tissue impedance load or tissue load. By varying the inductance of the saturable core reactor (SCR), the source impedance of the electrosurgical generator is dynamically adjusted under any surgical, operational or procedural conditions to offset the inductive or capacitive tissue load or tissue impedance load. Accordingly, if the load impedance or tissue impedance load is capacitive, the source impedance becomes more inductive or vice versa. Once the source and load impedances are matched, the tissue impedance load seen from the electrosurgical generator 10 is purely resistive. This matching condition in various embodiments leads to a resonance condition of the series LC tank circuit 30, which in turn, provides a zero-degrees phase shift between the RF output voltage and current of the generator.

Table I summarizes theoretical calculations illustrating the relationship between power efficiency and impedance matching of an exemplary electrosurgical system with and without an impedance matching network 300, e.g., the series LC tank or resonant circuit 30 with the SCR 302, according to the embodiments of the present invention. In this exemplary embodiment, the electrical characteristic, e.g., impedance, current, various powers: real power, reactive power and apparent power, and power factor are calculated for an exemplary inductive tissue impedance load or tissue load (i.e., $Z_{Load}$=50Ω+20 μH). As seen from Table I, with no impedance matching network, the calculated tissue impedance load is about 67Ω, creating a substantial mismatch with the 50Ω electrosurgical generator. The power factor is defined as the ratio of the real power (RF power provided by the electrosurgical generator to its output resistive tissue load) to the apparent power (RF power provided by the electrosurgical generator to its output complex tissue load). A high power factor (i.e., close to unity or "1") is indicative of lower power loss and higher efficiency. As seen from Table I, the calculated power efficiency is about 74.5% when no impedance matching is being performed between the source and load impedances.

TABLE I

Exemplary Embodiment of an Electrosurgical System with and without SCR (RF generator Output = 100 V/Tissue Impedance Load = 50Ω + 20 μH)

| Electrical Characteristics | Without SCR | With SCR |
|---|---|---|
| Impedance (Z) | 67Ω ∠ 41° | 50Ω ∠ 0° |
| Current (I) | 1.5 A | 2 A |
| Real Power (P) = $I^2 \cdot R$ | 112.5 W | 200 W |
| Reactive Power (Q) = $I^2 \cdot X$ | 99 VAR | 0 VAR |
| Apparent Power (S) = $I^2 \cdot Z$ | 151 VA | 200 VA |
| Power Factor (PF) = P/S | 74.5% | 100% |

In various embodiments, the inductance of saturable core reactor (SCR) 302 in the LC tank or resonant circuit 30 of the impedance matching network 300 is dynamically adjusted so that the source impedance of the electrosurgical generator is equal and opposite (complex conjugate) to the 20 μH tissue inductive load. This leads to a resonant condition in which the tissue impedance load or tissue load seen by the electrosurgical generator is purely resistive, i.e. the desired 50Ω target tissue load, leading to a power factor or power efficiency of 100%. It should be noted that these calculations are assuming no losses in the cables and connectors along the RF path of delivery. Accordingly, assuming ideal lossless conditions, the power efficiency has increased from the theoretical value of 74.5% with no SCR to 100% with the SCR impedance matching network.

In operation, in order to achieve this illustrative objective and not limited to such, a proportional-integral-derivative (PID) controller is used in combination with the saturable core reactor (SCR) 302 to form an impedance matching control module in accordance with various embodiments of the present invention. The focus of this control module is on the dynamic control of the inductance in the series LC tank or resonant circuit 30 to control the energy transfer efficiency between the electrosurgical generator 10 and the tissue impedance load or tissue load $Z_{Load}$ 20-1. The proportional-integral-derivative (PID) controller ensures an optimal matching of impedances based on sealing, fusing or cutting cycle of the tissue such that if the tissue impedance load or tissue load, e.g., load impedance, is capacitive, the source impedance becomes more inductive or vice versa. In addition, the speed and precision of impedance matching process in various embodiments are ensured by utilizing the PID (proportional-integral-derivative) control algorithm, circuitry or system.

Figure 6:
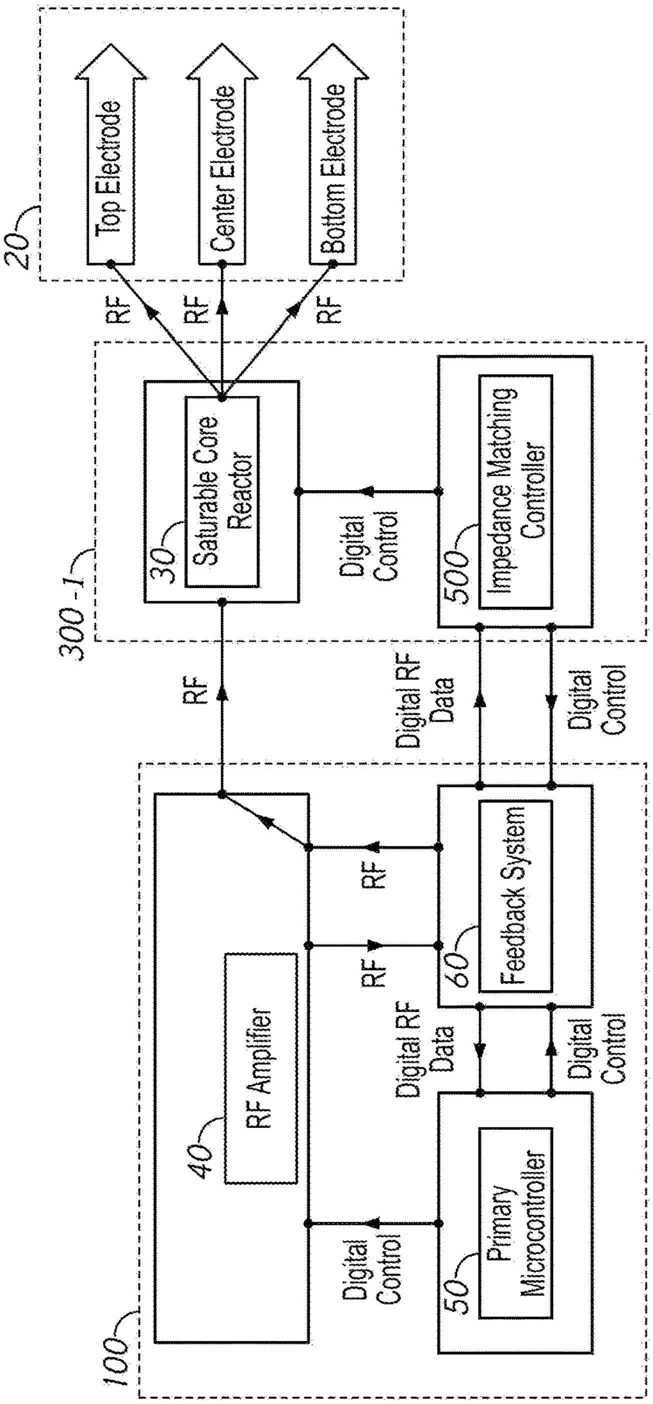
FIG. 6 illustrates a block diagram of an electrosurgical system depicting, in greater detail, an embodiment of a control system within an electrosurgical generator and an embodiment of an impedance matching network according to various embodiments of the present invention.

FIG. 6 illustrates a block diagram of an electrosurgical system depicting, in greater detail, an embodiment of a control system 100 of an electrosurgical generator and an embodiment of a control system 500 of an impedance matching network according to the embodiments of the present invention. In this embodiment, the impedance matching network 300-1 acts as a self-contained impedance matching module that operates independently of the electrosurgical generator 10. In accordance with various embodiments, the control system 100 provides regulation of RF output under dynamically changing impedance loads due to electrosurgical operations or electrosurgical tissues affects and/or impedance matching effects, and control conditions, e.g., device scripts or user operations. As such, the control system 100 in accordance with various embodiments is designed to adjust for different load impedances and output voltages and thus not limited to ideal conditions. The control system 100 is also configured to account for the system becoming over damped as impedance increases that can result in non-optimal phase margin and dynamic or unpredictable behavior and thus affect the ability of the control system 100 to track or follow dynamic commands, e.g., device script operations. The control system 100 of the generator in combination with the impedance matching network 300-1 ensures that tissue electrosurgical effects, such as for example, sealing, fusing or cutting, are optimized through critical responses of the control system to dynamically changing tissue impedance conditions and operational conditions and commands determined by the surgeon, surgical procedure and/or device script.

The servo control system 100 of the electrosurgical generator 10 in accordance with various embodiments may include the RF amplifier 40, the feedback system 60 and the primary microcontroller 50. The feedback system 60 creates a path for a closed-loop system between the RF amplifier 40 and the primary microcontroller 50. In various embodiments, the feedback system 60 may include three channels: a main channel, a redundant channel and a verification channel (not shown in FIG. 6). The main channel and redundant channel in various embodiments may include separate but identical components. Additionally, the main and redundant channels follow separate but identical electrical paths and in one embodiment are both connected to the RF amplifier 40 and the RF output. Similarly, components of the verification channel are separate from the main and redundant channels but are similar. In one embodiment, the verification channel may include the same components as the main and redundant channels, but the components in the verification channel have higher ratings, e.g., higher resolution and/or lower drift, and are often more costly. In another embodiment, the verification channel may include the same components as the main and redundant channels. The verification channel also follows a separate but identical electrical path as the main and redundant channels and in one embodiment is connected to the RF amplifier 40 and the RF output.

In various embodiments, the feedback system 60 measures analog RF output and digitizes the measurements. The feedback system 60 is configured to measure and digitize the RF output via at least one channel, e.g., main channel. In this embodiment, the feedback system 60 through the main channel measures the analog RF output via a front-end circuitry. The feedback system 60 in various embodiments collects its voltage and current measurements from the RF amplifier 40 and digitizes the measurements through analog to digital converters (ADC). The feedback system 60 is further configured to process the digitized values to derive real and imaginary components of the voltage and current RF output, and to communicate or transmit, e.g., serially, the real and imaginary components to the primary microcontroller 50 and PID controller 500.

The primary microcontroller 50 in accordance with various embodiments receives the digital real and imaginary components of the voltage and current measurements and calculates the magnitude of the voltage, current and power. In various embodiments, the primary microcontroller 50 further calculates individual error values for voltage, current and power and based on the error values determines or selects a regulation mode. Accordingly, the primary microcontroller 50 determines which of the three regulation mode, e.g., voltage, current and power, should be reinforced or activated by the electrosurgical generator 10. In various embodiments, the primary microcontroller 50 is further configured to generate an accumulated error value over time, for a selected RF regulation mode, and based on the previously calculated values compute a variable gain factor for each of the plurality of RF regulation modes to provide dynamic regulation of the variable or varying RF output of the generator 10. Additionally, since switching between voltage, current and power regulation modes occurs, the primary microcontroller 50 further performs a special preload calculation to allow for a gradual, non-disruptive transition in RF output. For a detailed discussion of the control system 100 of the electrosurgical generator 10, reference may be made to U.S. patent application Ser. No. 16/562,362, filed on Sep. 5, 2019, the content of which is incorporated by reference herein in its entirety.

Still referring to FIG. 6, the impedance matching network 300-1 is operatively coupled between the electrosurgical generator 10 and the electrosurgical device 20. As described further above and in accordance with various embodiments, the impedance matching network 300-1 may include a series LC tank or resonant circuit (variable resonant cell) 30 and an impedance matching controller or PID (proportional-integral-derivative) controller 500. In various embodiments, the series LC tank or resonant circuit 30 is comprised of a saturable core reactor (SCR) 302 coupled in series with a capacitor bank ($C_{Ser}$). The capacitor bank ($C_{Ser}$) may include one or more capacitors connected in series, parallel or any combination thereof to provide various load configuration or values. The PID controller 500, according to the embodiments of the present invention, may include a field-programmable gate array (FPGA) to process the received data, e.g., real and imaginary components of the voltage and current RF output, from the feedback system 60 and adjust the DC current flowing through the DC control winding of the SCR of the series LC tank or resonant circuit 30 to meet a desired resonant condition for matching the source and load impedances. This is achieved by continuously calculating an error value e(t) as the difference between a desired output value or setpoint and a measured variable value and applying a correction based on proportional (P), integral (I), and derivative (D) terms. In some embodiments, the desired output value or setpoint may be provided by a device script. In other embodiments, an advanced reduced instruction set machine (ARM) processor may be configured to establish the desired output value or setpoint. In accordance with various embodiments, the desired output value or setpoint is a zero-degrees phase shift and the measured value represents the phase measured between the RF output voltage and current of the generator.

Figure 7:
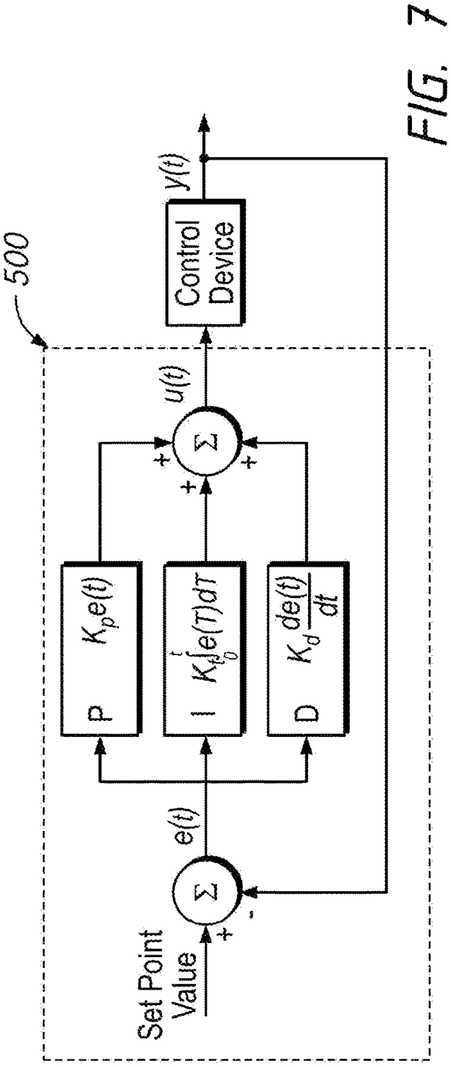
FIG. 7 is a schematic illustration of operational mode and functional block of a PID controller according to the embodiments of the present invention.

FIG. 7 is a schematic illustration of operational modes and functional blocks of a PID controller 500 of an impedance matching network 300-1 according to the embodiments of the present invention. In various embodiments, the FPGA of the PID controller 500 receives the measured real and imaginary voltage and current components or values from the feedback system 60 and uses these components to calculate the phase. The FPGA is further configured to calculate the relative error and based on the error value determines or selects a control output u(t) to adjust the phase between the RF output voltage and current. Accordingly, the control output u(t) in various embodiments sets the DC current flowing through the DC control windings of the saturable core reactor (SCR) 302 of the series LC tank or resonant circuit 30, which in turn controls the inductance of the SCR 302, to create a resonant condition for maximizing energy transfer efficiency between the electrosurgical generator 10 and the complex tissue impedance load or tissue load (i.e., the equivalent electrical circuit of the contact between the instrument 20 and the patient's body or surgical site). In various embodiments, the PID controller 500 ensures that tissue electrosurgical effects, such as for example, sealing, fusing or cutting, are optimized through critical response of the PID control system to dynamically changing tissue impedance conditions and operational conditions and commands determined by the surgeon, surgical procedure and/or device script. This is achieved by utilizing only the proportional (P) and integral (I) terms of the PID algorithm, circuitry or system to obtain the control output u(t) for adjusting the DC current that is flowing through the DC control winding of the saturable core reactor (SCR) 302, which in turn adjust the inductance of the SCR 302. By varying the inductance of the saturable core reactor (SCR) 302, the source impedance of the electrosurgical generator is dynamically adjusted under any surgical, operational or procedural conditions to offset the inductive or capacitive tissue impedance load or issue load, e.g., $Z_{Load}$ 20-1. Hence, resulting in an LC resonance condition which provides zero-degrees phase shift between the RF output voltage and current. As such, the total power in various embodiments gets delivered only across a resistive load, thereby maximizing RF energy transfer. Therefore, the impedance matching network 300-1, and in particular the PID controller 500, in accordance with various embodiments of the present invention, may act as a phase control loop and/or phase adjuster, providing critical step responses for all impedance load conditions or any changes thereto.

In an alternative embodiment, the electrosurgical generator 10 may include the impedance matching network 300. In this alternative embodiment, the impedance matching network 300 may be included or integrated into the control system 100 of the electrosurgical generator 10. In some embodiments, the SCR (saturable core reactor) module or the series LC tank/resonant circuit 30 may be included or integrated on the same circuit board as the RF amplifier 40. In other embodiments, the SCR module 30 may be included or integrated on a different circuit board that is positioned in series with the RF output circuit. In yet another embodiment, the SCR module 30 may be included or integrated on the same circuit board as the feedback system 60. In this alternative embodiment, where the impedance matching network, e.g., SCR module 30, is implemented within the electrosurgical generator 10, e.g., control system 100, the control loop algorithm, circuitry or system depicted in FIG. 7 of the present disclosure would be contained within the primary microcontroller 50. As such, a separate control mechanism, e.g., microcontroller 500, is no longer required for adjusting the DC current flowing through the DC control winding of the SCR module 30. As such and in accordance with various embodiments, the electrosurgical generator 10, after initiating the full device scripts, generates the required RF output energy. The feedback system 60 continuously monitors and measures the electrical properties, e.g., current and voltage of the RF energy directed across the one or more or all the channels of the feedback system 60 and digitally feeds the measured data to the primary microcontroller 50. The primary microcontroller 50, in accordance with various embodiments, is arranged to calculate the phase difference between the measured RF voltage with respect to the measured RF current. The PID control algorithm, circuitry or system, which in this embodiment is contained within the primary microcontroller 50, uses this phase to calculate the error, apply a gain and set a new output to control the DC current flowing through the DC control winding of the SCR module 30. The new set of digital controls will be communicated to the SCR module 30 which may be located on the same circuit board as the RF amplifier 40, on a different circuit board that is positioned in series with the RF output circuit or on the same circuit board as the feedback system 60.

Figure 8:
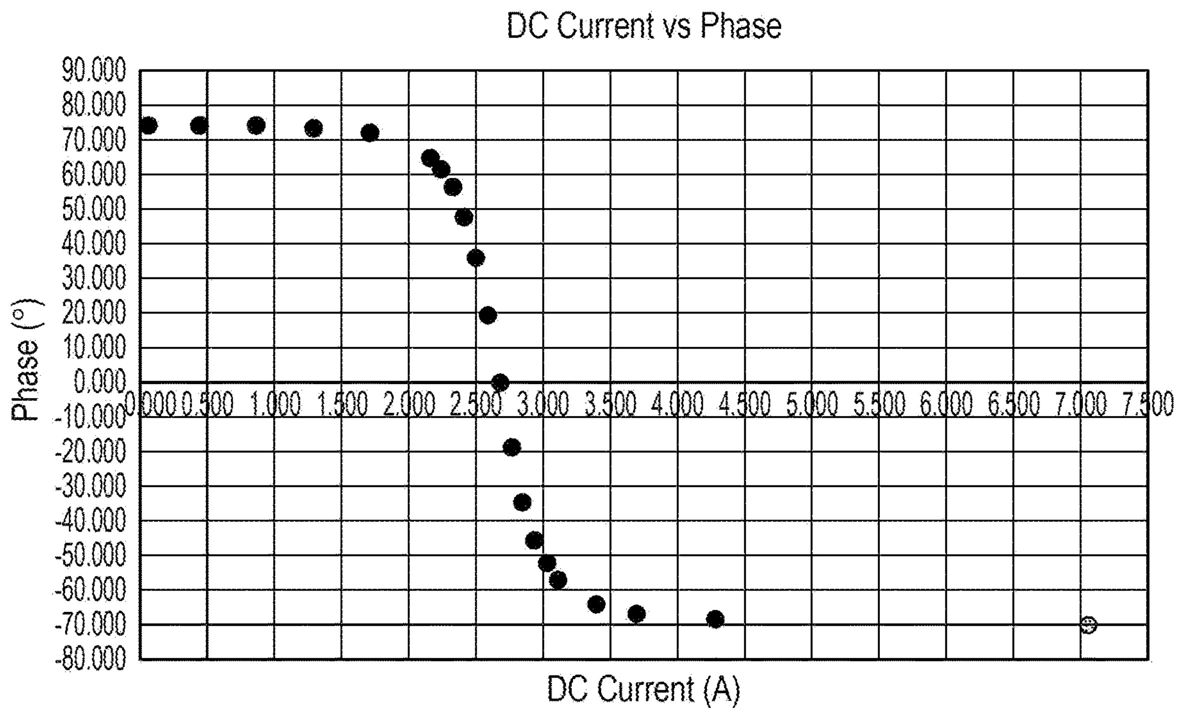
FIGS. 8-9 illustrate characteristics of a saturable core reactor (SCR) according to the embodiments of the present invention.
Figure 9:
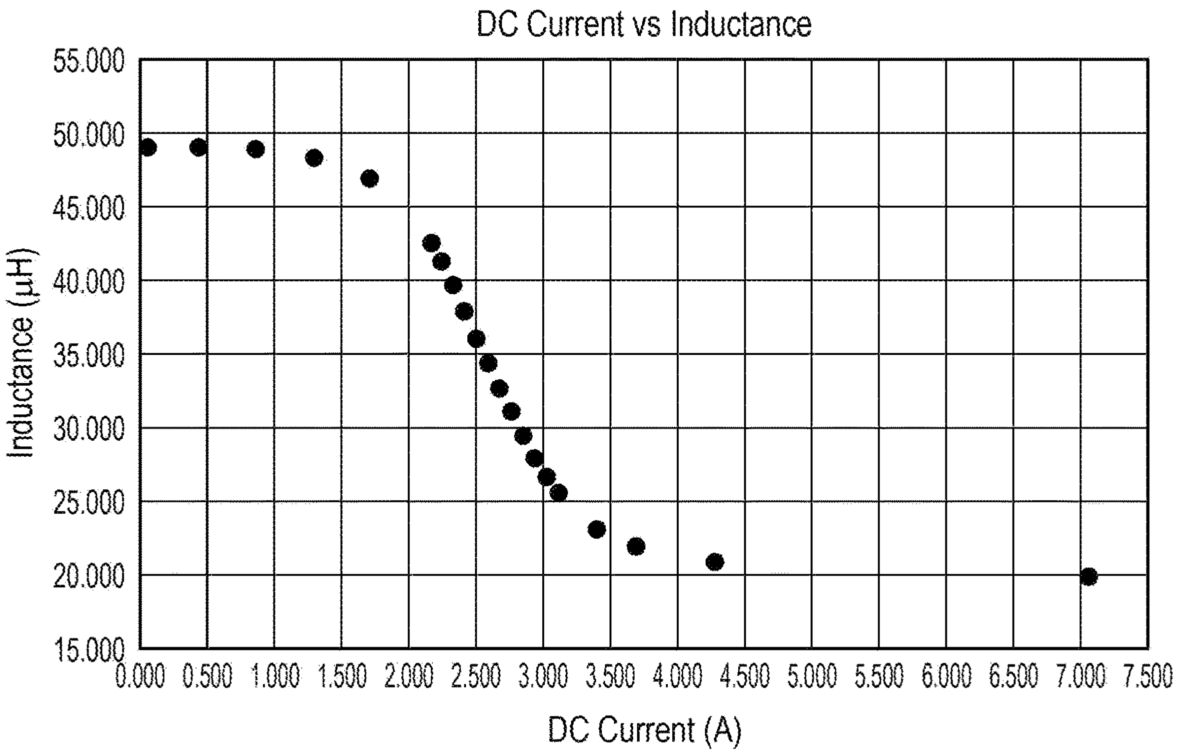

In what follows, the experimental results of an impedance matching network 300-1 according to the embodiments of the present invention will be explained in greater detail. For this purpose, an open loop characterization of the SCR (saturable core reactor) module 30 is first performed using a 10Ω resistive load and 20 Vrms RF output voltage. In accordance with various embodiments, the DC current, which is flowing through the DC control winding of the SCR module 30, is varied and the impedance of the AC winding of the SCR module 30 and the phase difference between the output RF voltage and current of the electrosurgical generator 10 are measured. FIGS. 8-9 are graphs illustrating respectively the SCR phase profile and the SCR inductance profile as a function of applied DC current in the DC control winding of the SCR module 30. As can be seen from these figures, the SCR phase profile shows a very inductive load when the applied DC current is approximately 0 A. As the applied DC current increases, the inductance of the AC winding of the SCR module 30 begins to decrease gradually. This results, in turn, in a gradual decrease of the inductive phase angle. The phase angle or phase difference between the RF output voltage and current becomes zero degrees at about 2.7 A where the RF output power is fully transferred across the 10Ω resistive load. Any further increase of the applied DC current beyond this value, will result in further decrease of the inductance of the AC winding of the SCR module 30, thereby causing a gradual increase of the capacitive phase angle. As shown in FIG. 8, the SCR phase profile shows a very capacitive load when the applied DC current is approximately 3.5 A. It should be noted that the range of inductance variation is about 50 μH to about 20 μH.

A closed-loop characterization of the SCR (saturable core reactor) module 30 is then performed using two different impedance loads. For this purpose, the SCR module 30 combined with the PID controller 500 is connected between the electrosurgical generator 10 and a complex tissue impedance load or tissue load. The tissue region in each of the impedance loads is modeled using a resistive load connected in series to a reactive load bank, e.g., a capacitive load or an inductive load. The electrosurgical generator 10 generates the required RF output energy and continuously measures the phase between the RF output voltage and current at an interval of 1 millisecond. The PID microcontroller 500 determines the error present between the measured phase and the setpoint value of the phase, e.g., zero-degrees phase. Based on the error value, the PID microcontroller 500 applies a gain and sets a new output to control the DC current flowing through the DC winding of the SCR (saturable core reactor) module 30. This new set of output is then communicated digitally to the SCR module 30 to adjust the inductance of the series LC tank or resonant circuit 30 and to progress towards having a zero servo-control error. The zero servo-control error indicates that the desired target setpoint, e.g., zero-degrees phase, has been reached and the impedance of the electrosurgical generator 10 has been matched with complex conjugate of the tissue impedance load or tissue load.

Figure 10:
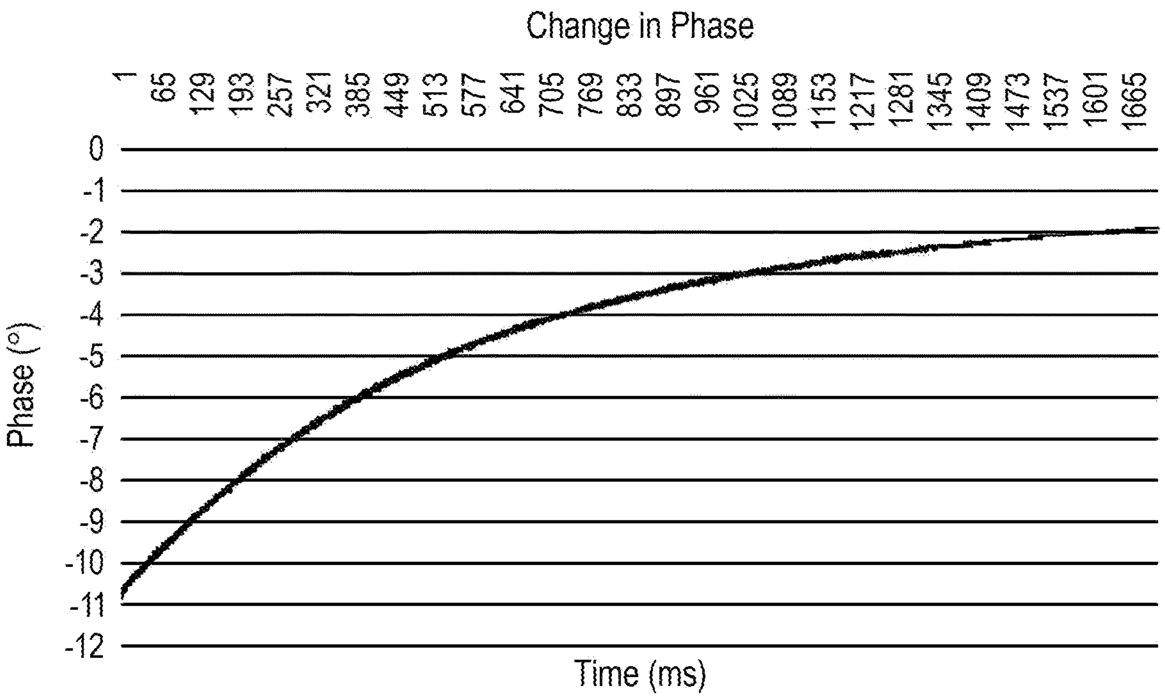
FIGS. 10-11 illustrate experimental results showing the change in phase and impedance of a saturable core reactor (SCR) across a capacitive load according to the embodiments of the present invention.
Figure 11:
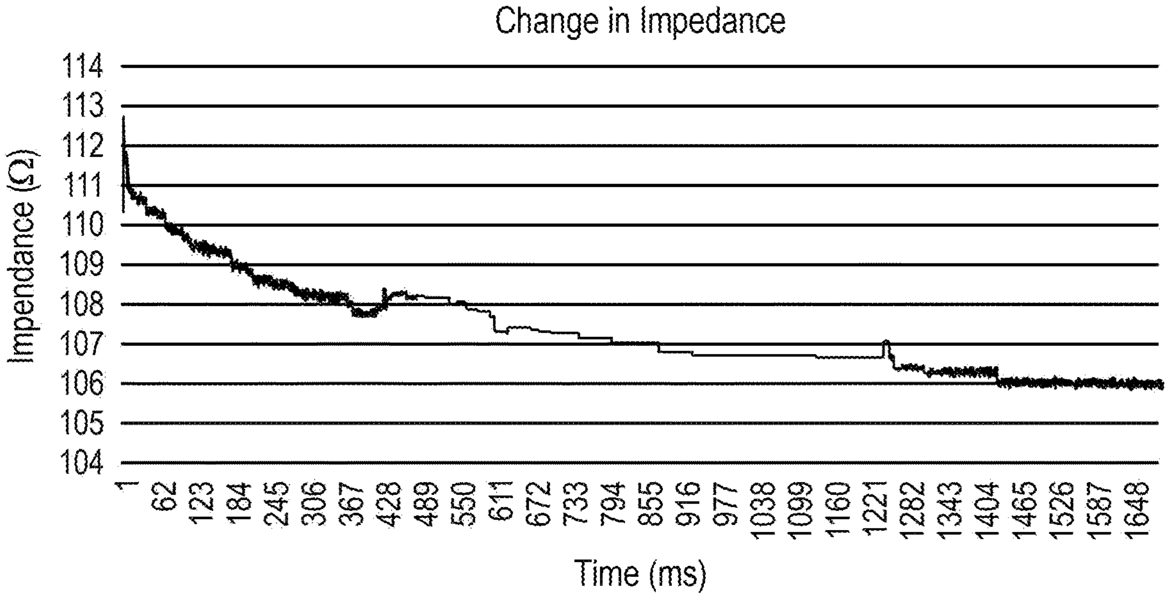

FIGS. 10-11 illustrate characteristics of the closed-loop SCR servo control system using an impedance load of $Z_{Load}$=100Ω+13.6 nF and 20 Vrms RF output voltage. More specifically, the SCR servo closed-loop response for achieving a setpoint of zero-degrees phase is shown in FIG. 10, while the SCR servo closed-loop impedance response for matching the source and load impedances is shown in FIG. 11. As can be seen from these figures, a substantial impedance mismatch is observed at the initial measurement point where the phase shift between the output RF voltage and current is about −10.6° and the measured impedance load is about 112.7Ω. Due to the resonance condition created by the SCR module 30, the phase shift between the RF output voltage and current gradually increases towards zero-degree phase, which is achieved at about −1.1°. At the same time, the impedance load seen from the electrosurgical generator 10 gradually decreases so that it changes from a capacitive load to a purely resistive load (source impedance is matched with complex conjugate of load impedance) which is achieved at about 105.3Ω. It is to be noted that the unwanted additional impedance at the final measurement point, e.g., 5.3Ω, may be attributed to impedance of cables, measuring wires, connectors and/or other components within the test setup.

Figure 12:
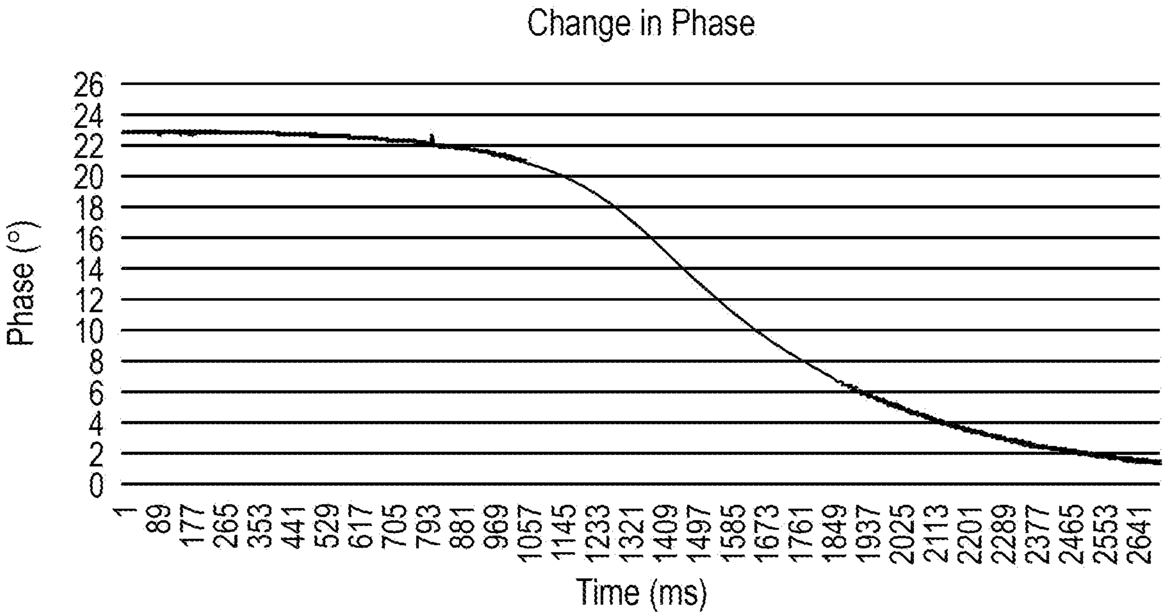
FIG. 12-13 illustrate experimental results showing the change in phase and impedance of a saturable core reactor (SCR) across an inductive load according to the embodiments of the present invention.
Figure 13:
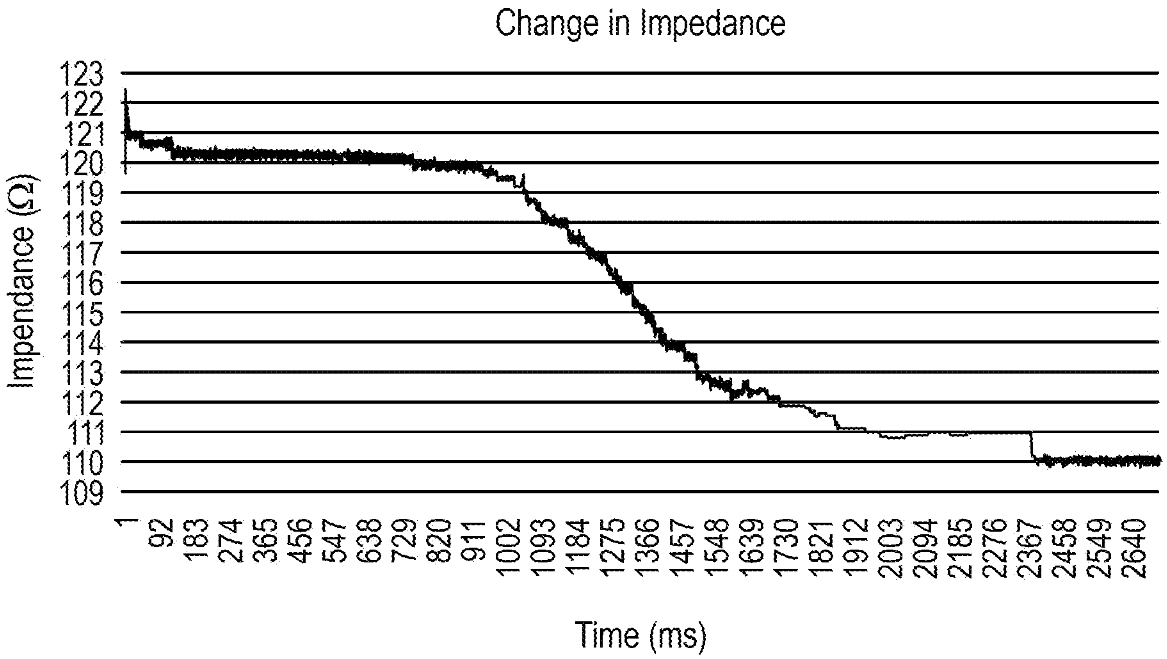

FIGS. 12-13 illustrate characteristics of the closed-loop SCR servo control system using an impedance load of $Z_{Load}$=100Ω+4.35 μH and 20 Vrms RF output voltage. Similar to the previous experimental results, the SCR servo-control loop response for achieving a setpoint of zero-degrees phase is shown in FIG. 12, while the SCR servo-closed loop impedance response for matching the source and load impedances is shown in FIG. 13. These results differ from that of FIGS. 10-11 in that the substantial impedance mismatch that is observed at the initial measurement points of (22.8°, 122.4Ω) stay approximately constant for a longer period of time (approximately 1 sec) prior to gradually decreasing towards a zero-degree phase shift and a purely resistive tissue impedance load or tissue load that is achieved at the final measurement points of (1.3°, 109.9Ω). In addition, the unwanted additional impedance at the final measurement point is slightly higher, e.g., 9.9Ω, compared to the previous measurement results. It is to be noted that the impedance load seen from the electrosurgical generator 10 changes from an inductive load at its initial measurement point to a purely resistive load at its final measurement point.

Table II summarizes measurement results and calculated electrical characteristics for both impedance loads at their respective initial and final measurements points. As can be seen from Table II, the power efficiency has improved from its initial value of 89% to its final value of 95% in the case of the capacitive complex impedance load. Similarly, the power efficiency has improved from its initial value of 83% to its final value of 92% in the case of the inductive complex impedance load. It should be noted that higher power efficiency may be attainable by implementing the entire test setup on a single PCBA (Printed Circuit Board Assembly) or circuit board. This allows for the reduction or elimination of unwanted additional impedance seen at the final measurement point that are added due to impedance of measuring wires, connectors and/or other components. It should be also noted that the measured AC current based on connected tissue impedance load for these experimental results was less than 1 A. Accordingly, for higher power applications that require higher RF current, the power efficiency improvement may also be higher.

TABLE II

Experimental Results of a Saturable Core Reactor Servo-Control Loop (RF generator Output = 20 Vrms)

| Electrical Characteristics | Z = 100 Ω + 13.6 nF | Z = 100 Ω + 4.35 μH |
|---|---|---|
| Initial Phase ($Ø_i$) | −10.6° | 22.8° |
| Initial Impedance ($Z_i$) | 112.7 Ω | 122.4 Ω |
| Initial Current ($I_i$) | 177 mA | 163 mA |
| Initial Real Power ($P_i$) = $I_i^2 \cdot R$ | 3.1 W | 2.7 W |
| Initial Apparent Power ($S_i$) = $I_i^2 \cdot Z_i$ | 3.5 W | 3.25 W |
| Initial Power Factor ($PF_i$) = $P_i/S_i$ | 89% | 83% |
| Final Phase ($Ø_f$) | −1.1° | −1.3° |
| Final Impedance ($Z_f$) | 105.3 Ω | 109.9 Ω |
| Final Current ($I_f$) | 190 mA | 182 mA |
| Final Real Power ($P_f$) = $I_f^2 \cdot R$ | 3.61 W | 3.3 W |
| Final Apparent Power ($PF_f$) = $I_f^2 \cdot Z_f$ | 3.8 W | 3.6 W |
| Final Power Factor ($PF_f$) = $P_f/S_f$ | 95% | 92% |

Figure 14:
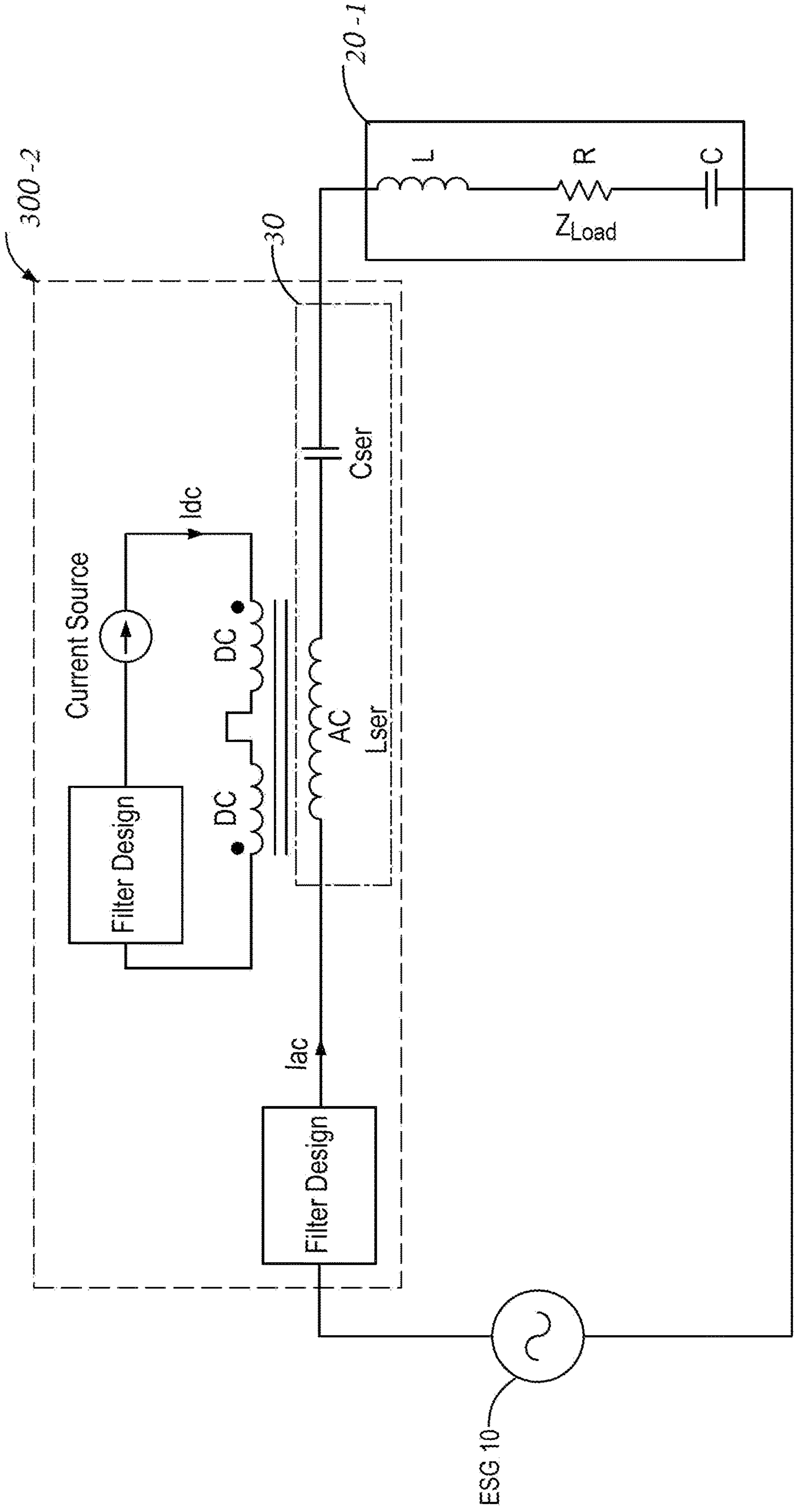
FIG. 14 illustrates an alternative embodiment of a saturable core reactor (SCR) according to the embodiments of the present invention.

Due to inconsistencies involved in the manufacturing process and the impedance matching network topology itself, e.g., saturable core reactor (SCR), some unwanted power components may couple from the AC load winding into the DC control winding, thereby creating unpredictable non-linearities in the inductive response. In an alternative embodiment, one or more filters, e.g., low pass filter, band-stop filter, or any other type of suitable filtering, may be added into the DC control winding and/or AC load winding of the SCR module 30 to reduce or eliminate these non-linearities in the response. This alternative embodiment allows for selectively filtering out any unwanted bands or regions of interfering frequencies. In some embodiments, the one or more filters may only be added to the DC control winding of the SCR module 30 to suppress higher frequency components that may couple from the AC load winding to the DC winding. FIG. 14 illustrates an alternative exemplary embodiment of a saturable core reactor (SCR) with the addition of one or more filters according to the embodiments of the present invention. Such alternative exemplary embodiments are contemplated to be within the scope of the present disclosure.

Figure 15A:
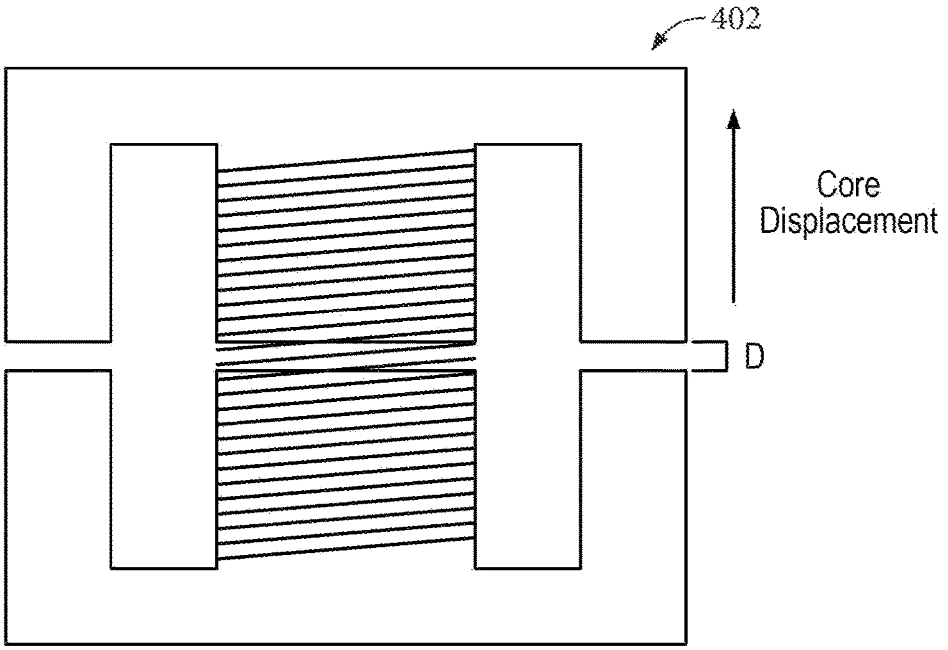
FIG. 15A-15B illustrate an alternative embodiment of an impedance matching network according to the embodiments of the present invention.
Figure 15B:
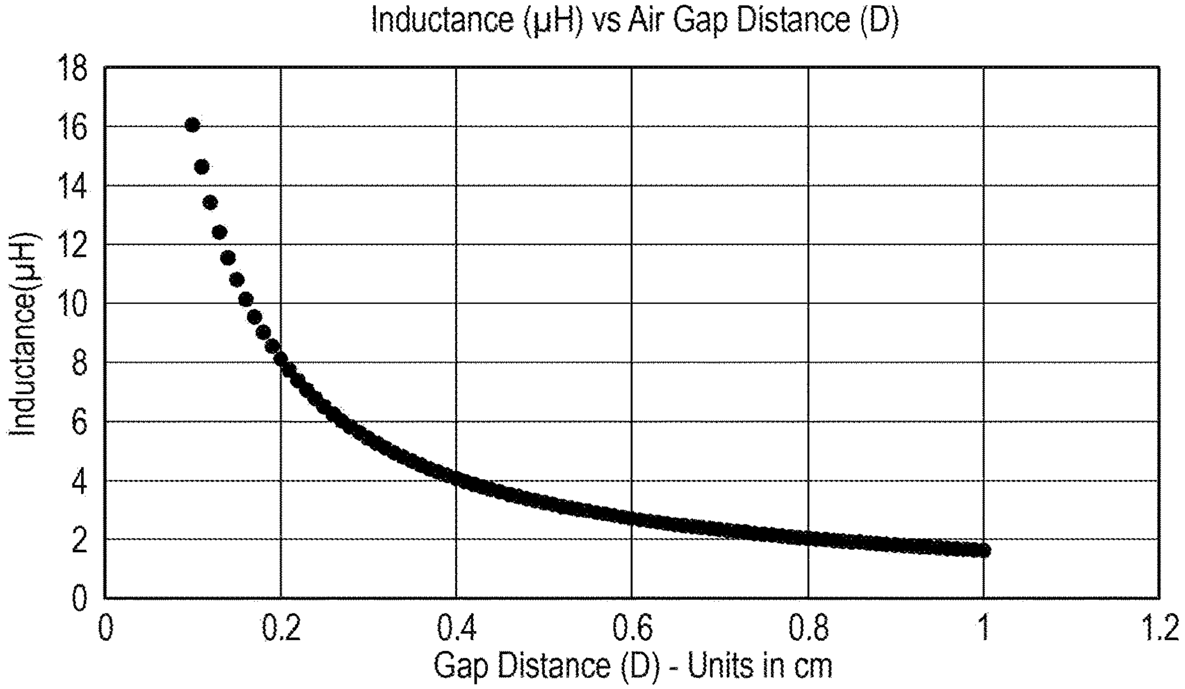

Referring next to FIGS. 15A-15B, another alternative embodiment of an impedance matching network 400 according to the embodiments of the present invention is shown. In this alternative embodiment, the impedance matching network may include a variable core inductor (VCI) 402. In various embodiments of the present invention, the variable core inductor (VCI) 402 is designed to dynamically adjust the inductance of the resonant cell 30, e.g., series LC tank/resonant circuit 30. This is achieved by moving a magnetic core in and out of an inductor. In essence, the VCI serves to vary the inductance of the resonant cell 30 through the manipulation or displacement of the magnetic core within the inductor. FIG. 15A depicts a schematic illustration of a variable core inductor (VCI) 402 according to the embodiments of the present invention. As can be seen from this figure, the magnetic core used in in this alternative embodiment may include two ETD (Economic Transformer Design) cores arranged in a symmetrically paired or mirror-image configuration where the two ETD cores are facing each other forming two identical halves. ETD cores have a distinctive E-shape with a cylindrical or circular central leg to maximize the magnetic flux path and facilitate efficient winding of coils. In accordance with various embodiments, a single central coil (best shown in FIG. 15A and also referred to by the "Inductor Bobbin/Winding" in FIG. 16) is wound around the central leg of the two ETD cores to form an adjustable inductor. In order to affect the inductance of the adjustable inductor, e.g., VCI (variable core inductor) 402, an air gap (i.e., distance D in FIG. 15A) may be created between the two identical halves of the EDT cores. By varying the position of one of the two identical halves, e.g., top half, relative to the other identical halves, e.g., bottom half, the air gap or distance D between the two ETD cores varies, thereby varying the inductance of the adjustable inductor or VCI 402. In accordance with various embodiments of the present invention by adjusting the inductance, the source and load impedances can be dynamically adjusted under any surgical, operational or procedural conditions to result in a resonant condition that provides zero-degrees phase shift between the RF output voltage and current of the generator, and hence maximizing RF energy transfer.

The inductance and air gap created between the two halves of the ETD cores are related by the effective permeability $\mu_e$ of the magnetic material as shown in the following equations:

$$L = \frac{4\pi N^2 \mu A}{\text{mL}} 10^{-3} (\mu H) \tag{1}$$

$$\mu_e = \frac{\mu_i}{1 + u_i\left(\frac{D}{\text{mL}}\right)} \tag{2}$$

where N represents the number of turns or windings in the single central coil, μ denotes permeability, A($cm^2$) signifies the cross-sectional area of the central leg of the ETD cores, mL (in cm) is the mean path length, $\mu_i$ stands for the initial permeability, and D/mL indicates the ratio of the gap to the length of the magnetic path. The above equations illustrate the dependency of the inductance on the size of the air gap in the inductor core material. That is, as one side of the core of the inductor, e.g., VCI (variable core inductor) 402, is displaced, e.g., top half of the ETD cores, the size of the air gap will increase, and the inductance will decrease proportional to the change in permeability.

FIG. 15B is a graph illustrating the inductance of the variable core inductor (VCI) as a function of the air gap according to the embodiments of the present invention. As shown in this figure, the inductance of the VCI (variable core inductor) inductor 402 gradually decreases as the distance or air gap between the two identical halves of the ETD cores increases. It is to be noted that the range of inductance variation is about 16 μH to about 1.6 μH for a core displacement of about 1 cm. As described further above and in accordance with various embodiments, by varying the inductance of the variable core inductor (VCI) 402, the source impedance of the electrosurgical generator is dynamically adjusted under any surgical, operational or procedural conditions to offset the inductive or capacitive tissue load or tissue impedance load. Accordingly, if the load impedance or tissue impedance load is capacitive, the source impedance becomes more inductive or vice versa. Once the source and load impedances are matched, the tissue impedance load seen from the electrosurgical generator is purely resistive. This matching condition in various embodiments leads to a resonance condition of the series LC tank or resonant circuit 30, which in turn, provides a zero-degrees phase shift between the RF output voltage and current.

Figure 16:
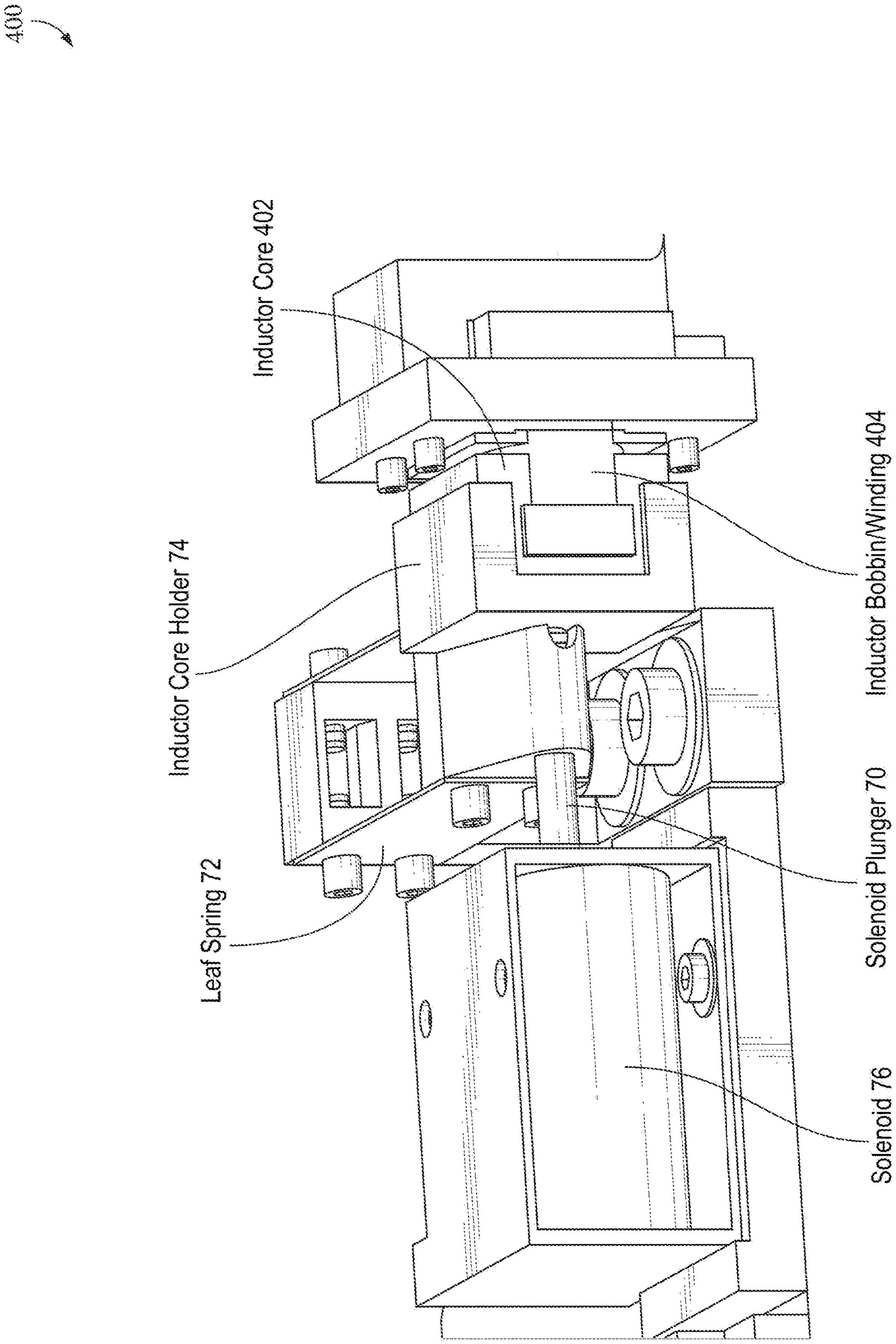
FIG. 16 illustrates a schematic implementation of a variable core inductor (VCI) module according to the embodiments of the present invention.

With reference to FIG. 16, a schematic implementation of a variable core inductor (VCI) module according to the embodiments of the present invention is shown. As depicted in this figure, the variation in the air gap is achieved by separating the two identical halves of the ETD cores. Additionally, it involves moving the top half of the ETD cores relative to its bottom half and adjusting their position in and out of the single central coil of the VCI inductor, identified by the inductor bobbin/winding 404. In various embodiments, precise control of the core positioning is attained by connecting a solenoid plunger 70 to a leaf spring 72, which is in turn linked to the top half of the two ETD cores of the VCI inductor 402. This assembly is secured within an inductor core holder 74. In accordance with various embodiments, a solenoid 76 is provided as the control mechanism for positioning or displacement of the top half of the two ETD cores. In various embodiments, the solenoid plunger's position is regulated by the solenoid current, which is a DC current flowing through the solenoid. Additionally, a permanent magnet positioned at the center of the solenoid plunger 70 contributes to the control of its position. The permanent magnet serves the purpose of introducing a constant or permanent positional offset. Consequently, the magnetic field generated by the current flowing through the solenoid 76 counteracts the permanent offset, ensuring precise position control of the solenoid plunger 70. In various embodiments, the leaf spring 72 imparts a predetermined stiffness to the system. This stiffness may increase as the solenoid plunger 70 is pushed progressively closer to the VCI inductor core, e.g., two ETD cores.

As described further above and in accordance with various embodiments, the inductance of the VCI (variable core inductor) 402 varies by adjusting the air gap (i.e., distance D) between the two ETD cores. Consequently, the phase difference between RF voltage and current can also undergoes variation. Accordingly, by adjusting the inductance, it becomes possible to match the source and load impedance (complex conjugates), thereby achieving higher power efficiency. In this alternative embodiment, the control parameter is the DC current flowing through the solenoid 76, which regulates the position of solenoid plunger 70. This movement, in turn, adjusts the position of the top half of the two ETD cores of the VCI inductor 402. It is to be noted that a successful operation of this alternative embodiment may depend greatly on mechanical arrangement of various parts which may be altered over time due to various factors such as, for example, vibration and/or mechanical alignment.

The above description is provided to enable any person skilled in the art to make and use the electrosurgical devices or systems and perform the methods described herein and sets forth the best modes contemplated by the inventors of carrying out their inventions. Various modifications, however, will remain apparent to those skilled in the art. It is contemplated that these modifications are within the scope of the present disclosure. Different embodiments or aspects of such embodiments may be shown in various figures and described throughout the specification. However, it should be noted that although shown or described separately each embodiment and aspects thereof may be combined with one or more of the other embodiments and aspects thereof unless expressly stated otherwise. It is merely for easing readability of the specification that each combination is not expressly set forth.

Although the present invention has been described in certain specific aspects, many additional modifications and variations would be apparent to those skilled in the art. It is therefore to be understood that the present invention may be practiced otherwise than specifically described, including various changes in the size, shape and materials, without departing from the scope and spirit of the present invention. Thus, embodiments of the present invention should be considered in all respects as illustrative and not restrictive.

What is claimed is:

1. An electrosurgical system for performing surgical procedures, comprising:

an electrosurgical generator configured to supply RF energy to a surgical site;

an electrosurgical instrument comprising at least one active electrode adapted to treat tissue with the supplied RF energy; and an impedance matching network comprising a tunable resonant cell interposed along a path of RF energy and arranged to provide maximum power transfer from the electrosurgical generator to the electrosurgical instrument by varying dynamically an inductance of the tunable resonant cell to create a resonant condition, thereby adjusting a phase of the supplied RF energy to a predetermined phase value, the tunable resonant cell comprising:

a variable core inductor (VCI) having a pair of E-shaped magnetic cores arranged in a mirror-image configuration forming a symmetrical structure having two identical halves; and a positional tuning mechanism configured to ensure precise control of a location of one of the two identical halves relative to the other, wherein the positional tuning mechanism comprises a solenoid having a solenoid plunger connected to said one of the two identical halves using a leaf spring.

2. The electrosurgical system of claim 1 wherein an airgap is formed between the two identical halves of the mirror-image configuration.

3. The electrosurgical system of claim 1 wherein each core of the pair of E-shaped magnetic cores comprises a central leg and two outer legs.

4. The electrosurgical system of claim 3 wherein the central leg in each core of the pair of E-shaped magnetic cores is cylindrical.

5. The electrosurgical system of claim 2 wherein an inductance of the VCI (variable core inductor) is adjustable in response to variations in a size of the airgap achieved by moving the one of the two identical halves relative to the other.

6. The electrosurgical system of claim 1 wherein the solenoid includes a permanent magnet configured to apply a constant positional offset between the two identical halves when a direct current (DC) is flowing through the solenoid.

7. The electrosurgical system of claim 6 wherein the permanent magnet is located at the center of solenoid plunger and the direct current (DC) is provided by a controller coupled to the impedance matching network.

8. The electrosurgical system of claim 7 wherein the controller is configured to selectively adjust a size of an airgap between the two identical halves by varying the magnitude of the direct current (DC) flowing through the solenoid based on an error value present between a measured phase of the supplied RF energy and the predetermined phase value.

9. The electrosurgical system of claim 7 wherein the controller receives measured voltage and current values of the supplied RF energy from a feedback system of the electrosurgical generator and calculates a phase difference between the measured voltage and current values of the supplied RF energy.

10. The electrosurgical system of claim 9 wherein the controller is configured to determine a phase error relative to the predetermined phase value to correct a phase shift between the voltage and current of the supplied RF energy, which results in setting the output to adjust the magnitude of the direct current (DC).

11. The electrosurgical system of claim 1 wherein the predetermined phase value is a zero-degree phase.

12. The electrosurgical system of claim 1 wherein in the mirror-image configuration the central leg and the two outer legs from each magnetic core are aligned and facing each other.

13. The electrosurgical system of claim 3 wherein the variable core inductor (VCI) comprises a single winding wound around the central leg of the mirror-image configuration.

14. The electrosurgical system of claim 1 wherein the variable core inductor (VCI) is coupled to a capacitor bank configured to provide multiple load configurations or load values.

* * * * *